US012642522B2

(12) United States Patent
Gilbert et al.

(10) Patent No.: US 12,642,522 B2
(45) Date of Patent: \*Jun. 2, 2026

(54) DEVICE AND METHOD FOR APPLYING A CINCH TO A SUTURE

(71) Applicant: BOSTON SCIENTIFIC SCIMED, INC., Maple Grove, MN (US)

(72) Inventors: Stan Robert Gilbert, Litchfield, NH (US); Shaun Dennis Comee, Fiskdale, MA (US); Peter Joseph Shank, Boylston, MA (US); Christopher R. Deuel, Melrose, MA (US); Dennis Brian Hubbard, Jr., Lancaster, MA (US); Norman C. May, Valrico, FL (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 94 days.

This patent is subject to a terminal disclaimer.

(21) Appl. No.: 18/830,757

(22) Filed: Sep. 11, 2024

(65) Prior Publication Data

US 2024/0423608 A1 Dec. 26, 2024

Related U.S. Application Data

(63) Continuation of application No. 18/097,401, filed on Jan. 16, 2023, now Pat. No. 12,114,852, which is a
(Continued)

(51) Int. Cl.
*A61B 17/04* (2006.01)

(52) U.S. Cl.
CPC ...... *A61B 17/0469* (2013.01); *A61B 17/0467* (2013.01); *A61B 17/0485* (2013.01); *A61B 2017/0496* (2013.01)

(58) Field of Classification Search
CPC ............ A61B 17/0467; A61B 17/0485; A61B 2017/0409; A61B 2017/0417; A61B 2017/045; A61B 2017/0488
See application file for complete search history.

(56) References Cited

U.S. PATENT DOCUMENTS 5,584,861 A  12/1996  Swain et al.
6,086,608 A   7/2000  Ek et al.
(Continued)

FOREIGN PATENT DOCUMENTS

JP       2014505519 A    3/2014

OTHER PUBLICATIONS

International Search Report and Written Opinion for Application No. PCT/US2019/033748, 16 pages, mailed Aug. 20, 2019.

*Primary Examiner* — Martin T Ton
(74) *Attorney, Agent, or Firm* — Seager, Tufte & Wickhem, LLP

(57) ABSTRACT

Medical devices for applying a cinch to a suture and methods for making and using such devices are disclosed. An example medical device may include an elongated shaft including a proximal region and a distal region. The distal region may define a lumen having a lumen dimeter, and a distally facing end surface. The medical device may also include an outer cinch member defining a bore and having an outer surface defining a shoulder. An elongated inner shaft may extend through and be longitudinally movable within the lumen and the bore and including a distal end section. An inner cinch member may be engaged with the distal end section of the elongated inner shaft.

17 Claims, 23 Drawing Sheets

Related U.S. Application Data continuation of application No. 16/420,804, filed on May 23, 2019, now Pat. No. 11,553,909.

(60) Provisional application No. 62/848,787, filed on May 16, 2019, provisional application No. 62/676,548, filed on May 25, 2018.

(56) References Cited

U.S. PATENT DOCUMENTS

| | | | |
|---|---|---|---|
| 6,200,329 B1 | 3/2001 | Fung et al. |
| 6,494,888 B1 | 12/2002 | Laufer et al. |
| 6,506,196 B1 | 1/2003 | Laufer |
| 6,554,845 B1 | 4/2003 | Fleenor et al. |
| 6,569,085 B2 | 5/2003 | Kortenbach et al. |
| 6,626,917 B1 | 9/2003 | Craig |
| 6,663,639 B1 | 12/2003 | Laufer et al. |
| 6,719,763 B2 | 4/2004 | Chung et al. |
| 6,740,030 B2 | 5/2004 | Martone et al. |
| 6,746,457 B2 | 6/2004 | Dana et al. |
| 6,755,843 B2 | 6/2004 | Chung et al. |
| 6,773,441 B1 | 8/2004 | Laufer et al. |
| 6,808,491 B2 | 10/2004 | Kortenbach et al. |
| 6,821,285 B2 | 11/2004 | Laufer et al. |
| 6,835,200 B2 | 12/2004 | Laufer et al. |
| 6,908,427 B2 | 6/2005 | Fleener et al. |
| 6,997,931 B2 | 2/2006 | Sauer et al. |
| 7,056,284 B2 | 6/2006 | Martone et al. |
| 7,063,710 B2 | 6/2006 | Takamoto et al. |
| 7,063,715 B2 | 6/2006 | Onuki et al. |
| 7,094,246 B2 | 8/2006 | Anderson et al. |
| 7,144,401 B2 | 12/2006 | Yamamoto et al. |
| 7,147,646 B2 | 12/2006 | Dana et al. |
| 7,153,314 B2 | 12/2006 | Laufer et al. |
| 7,220,266 B2 | 5/2007 | Gambale |
| 7,232,445 B2 | 6/2007 | Kortenbach et al. |
| 7,235,086 B2 | 6/2007 | Sauer et al. |
| 7,326,221 B2 | 2/2008 | Sakamoto et al. |
| 7,344,545 B2 | 3/2008 | Takemoto et al. |
| 7,347,863 B2 | 3/2008 | Rothe et al. |
| 7,361,180 B2 | 4/2008 | Saadat et al. |
| 7,530,985 B2 | 5/2009 | Takemoto et al. |
| 7,601,161 B1 | 10/2009 | Nobles et al. |
| 7,618,425 B2 | 11/2009 | Yamamoto et al. |
| 7,713,277 B2 | 5/2010 | Laufer et al. |
| 7,722,633 B2 | 5/2010 | Laufer et al. |
| 7,727,246 B2 | 6/2010 | Sixto, Jr. et al. |
| 7,736,373 B2 | 6/2010 | Laufer et al. |
| 7,776,057 B2 | 8/2010 | Laufer et al. |
| 7,776,066 B2 | 8/2010 | Onuki et al. |
| 7,842,051 B2 | 11/2010 | Dana et al. |
| 7,846,180 B2 | 12/2010 | Cerier |
| 7,857,823 B2 | 12/2010 | Laufer et al. |
| 7,896,893 B2 | 3/2011 | Laufer et al. |
| 7,918,867 B2 | 4/2011 | Dana et al. |
| 7,951,157 B2 | 5/2011 | Gambale |
| 7,992,571 B2 | 8/2011 | Gross et al. |
| 7,993,368 B2 | 8/2011 | Gambale et al. |
| 8,016,840 B2 | 9/2011 | Takemoto et al. |
| 8,021,376 B2 | 9/2011 | Takemoto et al. |
| 8,057,494 B2 | 11/2011 | Laufer et al. |
| 8,062,314 B2 | 11/2011 | Sixto, Jr. et al. |
| 8,066,721 B2 | 11/2011 | Kortenbach et al. |
| 8,105,355 B2 | 1/2012 | Page et al. |
| 8,211,123 B2 | 7/2012 | Gross et al. |
| 8,216,253 B2 | 7/2012 | Saadat et al. |
| 8,226,667 B2 | 7/2012 | Viola et al. |
| 8,277,468 B2 | 10/2012 | Laufer et al. |
| 8,287,554 B2 | 10/2012 | Cerier et al. |
| 8,287,556 B2 | 10/2012 | Gilkey et al. |
| 8,308,765 B2 | 11/2012 | Saadat et al. |
| 8,313,496 B2 | 11/2012 | Sauer et al. |
| 8,361,089 B2 | 1/2013 | Chu |
| 8,388,632 B2 | 3/2013 | Gambale |
| 8,425,555 B2 | 4/2013 | Page et al. |
| 8,454,631 B2 | 6/2013 | Viola et al. |
| 8,480,691 B2 | 7/2013 | Dana et al. |
| 8,540,735 B2 | 9/2013 | Mitelberg et al. |
| 8,551,120 B2 | 10/2013 | Gambale |
| 8,585,720 B2 | 11/2013 | Gross et al. |
| 8,632,553 B2 | 1/2014 | Sakamato et al. |
| 8,679,136 B2 | 3/2014 | Mitelberg |
| 8,764,771 B2 | 7/2014 | Chu |
| 8,882,785 B2 | 11/2014 | DiCesare et al. |
| 8,926,634 B2 | 1/2015 | Rothe et al. |
| 8,992,570 B2 | 3/2015 | Gambale et al. |
| 9,011,466 B2 | 4/2015 | Adams et al. |
| 9,089,325 B2 | 7/2015 | Mitelberg et al. |
| 9,125,646 B2 | 9/2015 | Woodard, Jr. et al. |
| 9,198,562 B2 | 12/2015 | Mitelberg et al. |
| 9,320,515 B2 | 4/2016 | Dana et al. |
| 9,486,126 B2 | 11/2016 | West et al. |
| 9,504,465 B2 | 11/2016 | Chu |
| 9,510,817 B2 | 12/2016 | Saadat et al. |
| 9,549,728 B2 | 1/2017 | Chu |
| 9,750,494 B2 | 9/2017 | Gross et al. |
| 9,788,831 B2 | 10/2017 | Mitelberg |
| 9,844,366 B2 | 12/2017 | Woodard, Jr. et al. |
| 9,867,610 B2 | 1/2018 | Mitelberg et al. |
| 10,045,871 B2 | 8/2018 | Saadat et al. |
| 10,143,463 B2 | 12/2018 | Dana et al. |
| 10,194,902 B2 | 2/2019 | Nobles et al. |
| 10,335,142 B2 | 7/2019 | Raybin et al. |
| 2003/0204205 A1 | 10/2003 | Sauer et al. |
| 2004/0002699 A1 | 1/2004 | Ryan et al. |
| 2005/0250985 A1 | 11/2005 | Saadat et al. |
| 2007/0270908 A1* | 11/2007 | Stokes ............... A61B 17/0487 606/232 |
| 2008/0086148 A1 | 4/2008 | Baker et al. |
| 2008/0234729 A1* | 9/2008 | Page ................. A61B 17/0487 606/232 |
| 2010/0137681 A1 | 6/2010 | Ewers et al. |
| 2012/0158023 A1* | 6/2012 | Mitelberg .......... A61B 17/0485 606/144 |
| 2012/0271327 A1 | 10/2012 | West et al. |
| 2013/0096581 A1 | 4/2013 | Gilkey et al. |
| 2013/0304093 A1 | 11/2013 | Serina et al. |
| 2014/0128668 A1 | 5/2014 | Cox et al. |
| 2015/0126983 A1 | 5/2015 | Alvarado et al. |
| 2016/0045197 A1 | 2/2016 | Mitelberg et al. |
| 2017/0042534 A1 | 2/2017 | Nobles et al. |
| 2017/0086817 A1 | 3/2017 | Mitelberg |
| 2017/0086818 A1 | 3/2017 | Mitelberg |
| 2017/0119371 A1 | 5/2017 | Mims et al. |
| 2017/0319197 A1 | 11/2017 | Gross et al. |
| 2018/0042602 A1 | 2/2018 | Mitelberg et al. |
| 2018/0042603 A1 | 2/2018 | Mitelberg et al. |
| 2018/0221009 A1 | 8/2018 | Mitelberg et al. |
| 2018/0344501 A1 | 12/2018 | Saadat et al. |
| 2019/0209160 A1 | 7/2019 | Mitelberg et al. |

* cited by examiner

DEVICE AND METHOD FOR APPLYING A CINCH TO A SUTURE

CROSS-REFERENCE TO RELATED APPLICATIONS

This application is a continuation of and claims the benefit of the earlier filing date of U.S. patent application Ser. No. 18,097,401, filed Jan. 16, 2023, which is a continuation of U.S. patent application Ser. No. 16/420,804, filed May 23, 2019, now U.S. Pat. No. 11,553,909; which claims the benefit of priority of U.S. Provisional Application No. 62/848,787, filed May 16, 2019, and U.S. Provisional Application No. 62/676,548, filed May 25, 2018, and which applications are incorporated herein by reference in their entireties for all purposes. Any and all priority claims identified in the Application Data Sheet, or any correction thereto, are hereby incorporated by reference under 37 C.F.R. § 1.57.

TECHNICAL FIELD

The present disclosure pertains to medical devices, and methods for manufacturing medical devices. More particularly, the present disclosure pertains to devices for applying a cinch to a suture, and methods for manufacturing and using such devices.

BACKGROUND

A wide variety of medical devices and methods have been developed for suturing tissue, and securing and/or terminating the free end of a suture relative to the tissue once a suture is in place. These devices are manufactured by any one of a variety of different manufacturing methods and may be used according to any one of a variety of methods. Of the known devices and methods, each has certain advantages and disadvantages. There is an ongoing need to provide alternative devices as well as alternative methods for manufacturing and using such devices.

SUMMARY

This disclosure provides design, material, manufacturing method, and use alternatives for suture termination devices, for example, devices for applying a cinch to a suture.

In some embodiments, the medical device comprises: an elongated shaft including a proximal region and a distal region, the distal region defining a lumen having a lumen dimeter, and a distally facing end surface; an outer cinch member defining a bore and having an outer surface defining a shoulder, the shoulder having a proximally facing shoulder surface and having a shoulder diameter greater than the lumen dimeter, wherein the outer cinch member includes a proximal portion that is proximal of the shoulder, the outer cinch member having a first configuration wherein the proximal portion is disposed within the lumen and is engaged with the distal region of the elongate shaft and a gap is defined between the proximally facing shoulder surface and the distally facing end surface; an elongated inner shaft extending through and longitudinally movable within the lumen and the bore and including a distal end section; and an inner cinch member engaged with the distal end section of the elongated inner shaft, the inner cinch member configured to engage the outer cinch member and including at least a segment configured to fit within the bore.

In some embodiments, the medical device comprises: an elongated shaft including a proximal region and a distal region, the distal region defining a lumen having a lumen dimeter, and a distally facing end surface; an outer cinch member defining a bore and having an outer surface defining a shoulder, the shoulder having a proximally facing shoulder surface and having a shoulder diameter greater than the lumen dimeter, wherein the outer cinch member includes a proximal portion that is proximal of the shoulder, the outer cinch member having a first configuration wherein the proximal portion is disposed within the lumen and is engaged with the distal region of the elongate shaft with a frangible bond and a gap is defined between the proximally facing shoulder surface and the distally facing end surface; an elongated inner shaft extending through and longitudinally movable within the lumen and the bore and including a distal end section; and an inner cinch member engaged with the distal end section of the elongated inner shaft, the inner cinch member configured to engage the outer cinch member and including at least a segment configured to fit within the bore.

Alternatively or additionally to any of the embodiments above or below, the elongated inner shaft is designed such that proximal longitudinal movement of elongated inner shaft moves the inner cinch member into engagement with the outer cinch member.

Alternatively or additionally to any of the embodiments above or below, wherein the outer cinch member is designed to shift toward a second configuration where the proximally facing shoulder surface engages the distally facing end surface of the elongated shaft.

Alternatively or additionally to any of the embodiments above or below, in the first configuration the outer cinch member is engaged with the distal region of the elongate shaft with a bond; and in the second configuration, the bond is released.

Alternatively or additionally to any of the embodiments above or below, the elongated inner shaft is designed such that proximal longitudinal movement of the elongated inner shaft shifts the outer cinch member from the first configuration toward the second configuration.

Alternatively or additionally to any of the embodiments above or below, the proximal portion of the outer cinch member is engaged with the distal region of the elongate shaft with a frangible bond.

Alternatively or additionally to any of the embodiments above or below, the outer cinch member is designed to shift toward a second configuration where the frangible bond between the outer cinch member and the distal region is broken.

Alternatively or additionally to any of the embodiments above or below, the outer cinch member is designed to shift toward a second configuration where the frangible bond between the outer cinch member and the distal region is broken and the proximally facing shoulder surface engages the distally facing end surface of the elongated shaft.

Alternatively or additionally to any of the embodiments above or below, when in the second configuration the proximally facing shoulder surface engages the distally facing end surface of the elongated shaft.

Alternatively or additionally to any of the embodiments above or below, further including a suture cutting member disposed within the lumen of the distal region, and wherein the elongated inner shaft is designed to engage the suture cutting member for cutting the suture.

Alternatively or additionally to any of the embodiments above or below, the elongated inner shaft is designed such that a first stage of proximal longitudinal movement of the elongated inner shaft moves the inner cinch member into engagement with the outer cinch member, and a second stage of proximal longitudinal movement of the elongated inner shaft shifts the outer cinch member toward a second configuration in which the proximally facing shoulder surface engages the distally facing end surface of the elongated shaft.

Alternatively or additionally to any of the embodiments above or below, the elongated inner shaft is designed such that a first stage of proximal longitudinal movement of the elongated inner shaft moves the inner cinch member into engagement with the outer cinch member, and a second stage of proximal longitudinal movement of the elongated inner shaft breaks the frangible bond and shifts the outer cinch member toward a second configuration in which the proximally facing shoulder surface engages the distally facing end surface of the elongated shaft.

Alternatively or additionally to any of the embodiments above or below, the elongated inner shaft is designed such that a third stage of proximal movement of the elongated inner shaft disengages the elongated inner shaft from the inner cinch member.

Alternatively or additionally to any of the embodiments above or below, further including a suture cutting member disposed within the lumen of the distal region, and the elongated inner shaft is designed such that a fourth stage of proximal movement of the elongated inner shaft engages the elongated inner shaft with the suture cutting member.

Alternatively or additionally to any of the embodiments above or below, further including: a cutout defined in the distal region of the elongated shaft defining a distally facing shear edge; and a suture cutting member disposed within the lumen and including a proximally facing shear edge, the suture cutting member having an open configuration wherein the proximally facing shear edge is disposed distally of the distally facing shear edge to define an opening between the proximally facing shear edge and the distally facing shear edge, and wherein the suture cutting member is designed to shift toward a closed configuration where the proximally facing shear edge has moved proximally relative to the distally facing shear edge such that the opening is closed.

Alternatively or additionally to any of the embodiments above or below, further including: a shear member affixed within the lumen and defining a distally facing shear edge; and a suture cutting member disposed within the lumen and including a proximally facing shear edge, the suture cutting member having an open configuration wherein the proximally facing shear edge is disposed distally of the distally facing shear edge to define an opening between the proximally facing shear edge and the distally facing shear edge, and wherein the suture cutting member is designed to shift toward a closed configuration where the proximally facing shear edge has moved proximally relative to the distally facing shear edge such that the opening is closed.

Alternatively or additionally to any of the embodiments above or below, the elongated inner shaft is designed such that proximal longitudinal movement of elongated inner shaft shifts the suture cutting member from the open configuration toward the closed configuration.

Alternatively or additionally to any of the embodiments above or below, in the open configuration the suture cutting member is engaged with the distal region of the elongate shaft with a frangible bond.

Alternatively or additionally to any of the embodiments above or below, in the closed configuration, the frangible bond between the suture cutting member and the distal region is broken.

Alternatively or additionally to any of the embodiments above or below, the shear member is a tubular member defining a shear member lumen having an inner diameter, and wherein the suture cutting member is a tubular member having an outer diameter sized to fit within the inner diameter of the shear member lumen.

Alternatively or additionally to any of the embodiments above or below, the suture cutting member is a tubular member including a cutout portion forming the proximally facing shear edge.

A medical device for applying a cinch to a suture is disclosed. In some embodiments, the medical device comprises: an elongated shaft including a proximal region and a distal region, the distal region defining a lumen, and a distally facing end surface; an outer cinch member defining a bore, and a shoulder having a proximally facing shoulder surface, wherein the outer cinch member includes a proximal portion disposed within the lumen and is releasably engaged with the distal region of the elongate shaft such that the shoulder is spaced distally from the distally facing end surface; an elongated inner shaft extending through the lumen and the bore and including a distal end section; an inner cinch member engaged with the distal end section of the elongated inner shaft, the inner cinch member configured to engage the outer cinch member and includes at least a segment configured to fit within the bore; a distally facing shear edge defined by the distal region of the elongated shaft; and a suture cutting member disposed within the lumen and including a proximally facing shear edge, the suture cutting member having an open configuration wherein the proximally facing shear edge is disposed distally of the distally facing shear edge to define an opening between the proximally facing shear edge and the distally facing shear edge.

In some embodiments, the medical device comprises: an elongated shaft including a proximal region and a distal region, the distal region defining a lumen; an outer cinch member defining a bore, wherein the outer cinch member includes a proximal portion disposed within the lumen and is releasably engaged with the distal region of the elongate shaft; an elongated inner shaft extending through the lumen and the bore and including a distal end section; an inner cinch member engaged with the distal end section of the elongated inner shaft, the inner cinch member configured to engage the outer cinch member and includes at least a segment configured to fit within the bore; a shear member affixed within the lumen and defining a distally facing shear edge; and a suture cutting member disposed within the lumen and including a proximally facing shear edge, the suture cutting member having an open configuration wherein the proximally facing shear edge is disposed distally of the distally facing shear edge to define an opening between the proximally facing shear edge and the distally facing shear edge.

Alternatively or additionally to any of the embodiments above or below, the suture cutting member is designed to shift toward a closed configuration where the proximally facing shear edge has moved proximally relative to the distally facing shear edge such that the opening is closed.

Alternatively or additionally to any of the embodiments above or below, the elongated inner shaft is designed such that proximal longitudinal movement of elongated inner shaft shifts the suture cutting member from the open configuration toward the closed configuration.

Alternatively or additionally to any of the embodiments above or below, in the open configuration the suture cutting member is engaged with the distal region of the elongate shaft with a frangible bond.

Alternatively or additionally to any of the embodiments above or below, in the closed configuration, the frangible bond is broken.

Alternatively or additionally to any of the embodiments above or below, in the open configuration the suture cutting member is engaged with the distal region of the elongate shaft with a bond; and in the closed configuration, the bond is released.

Alternatively or additionally to any of the embodiments above or below, the suture cutting member is a tubular member having an outer diameter sized to slidably fit with a tight tolerance within the lumen of the distal region of the elongated shaft.

Alternatively or additionally to any of the embodiments above or below, the shear member is a tubular member defining a shear member lumen, and wherein the suture cutting member is a tubular member having an outer diameter sized to fit within the shear member lumen.

Alternatively or additionally to any of the embodiments above or below, the suture cutting member is a tubular member having a cutout portion forming the proximally facing shear edge.

A method for applying a cinch to a suture is disclosed. Some embodiments include a method for applying a cinch to a suture using a medical device, the medical device including: an elongated shaft having a distal region defining a lumen and a distally facing end surface; an outer cinch member defining a bore and including an outer surface defining a shoulder having a proximally facing shoulder surface, the outer cinch member having a first configuration where the outer cinch member is engaged with the distal region of the elongate shaft and a gap is defined between the proximally facing shoulder surface and the distally facing end surface; an elongated inner shaft extending through and longitudinally movable within the lumen and the bore and including a distal end section; and an inner cinch member which is engaged with the distal end section of the elongated inner shaft; and the method comprising: passing a length of the suture through the bore of the outer cinch member and between the outer cinch member and the inner cinch member while the outer cinch member is in the first configuration and the inner cinch member is disengaged from the outer cinch member; moving the elongated inner shaft proximally through a first stage of proximal longitudinal movement such that the inner cinch member engages the outer cinch member, thereby trapping a portion of the suture there between; and moving the elongated inner shaft proximally through a second stage of proximal longitudinal movement to shift the outer cinch member toward a second configuration where the proximally facing shoulder of the outer cinch member engages the distally facing end surface of the elongated shaft.

A method for applying a cinch to a suture using a medical device, the medical device including: an elongated shaft having a distal region defining a lumen and a distally facing end surface; an outer cinch member defining a bore and including an outer surface defining a shoulder having a proximally facing shoulder surface, the outer cinch member having a first configuration where the outer cinch member is engaged with the distal region of the elongate shaft with a frangible bond and a gap is defined between the proximally facing shoulder surface and the distally facing end surface; an elongated inner shaft extending through and longitudinally movable within the lumen and the bore and including a distal end section; and an inner cinch member which is engaged with the distal end section of the elongated inner shaft; the method comprising: passing a length of the suture through the bore of the outer cinch member and between the outer cinch member and the inner cinch member while the outer cinch member is in the first configuration and the inner cinch member is disengaged from the outer cinch member; moving the elongated inner shaft proximally through a first stage of proximal longitudinal movement such that the inner cinch member engages the outer cinch member, thereby trapping a portion of the suture there between; and moving the elongated inner shaft proximally through a second stage of proximal longitudinal movement to shift the outer cinch member toward a second configuration where the frangible bond between the outer cinch member and the distal region is broken and the proximally facing shoulder of the outer cinch member engages the distally facing end surface of the elongated shaft.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which:

FIG. 6 is a side cross-sectional view of a portion of the medical device of FIG. 5, where the inner shaft has been moved proximally, and the inner and outer cinch members are engaged, securing the suture there between;

FIG. 10 is a side cross-sectional view of the cinch anchoring a suture that extends through tissue, including the inner and outer cinch members are engaged and securing the suture there between;

Figure 1:
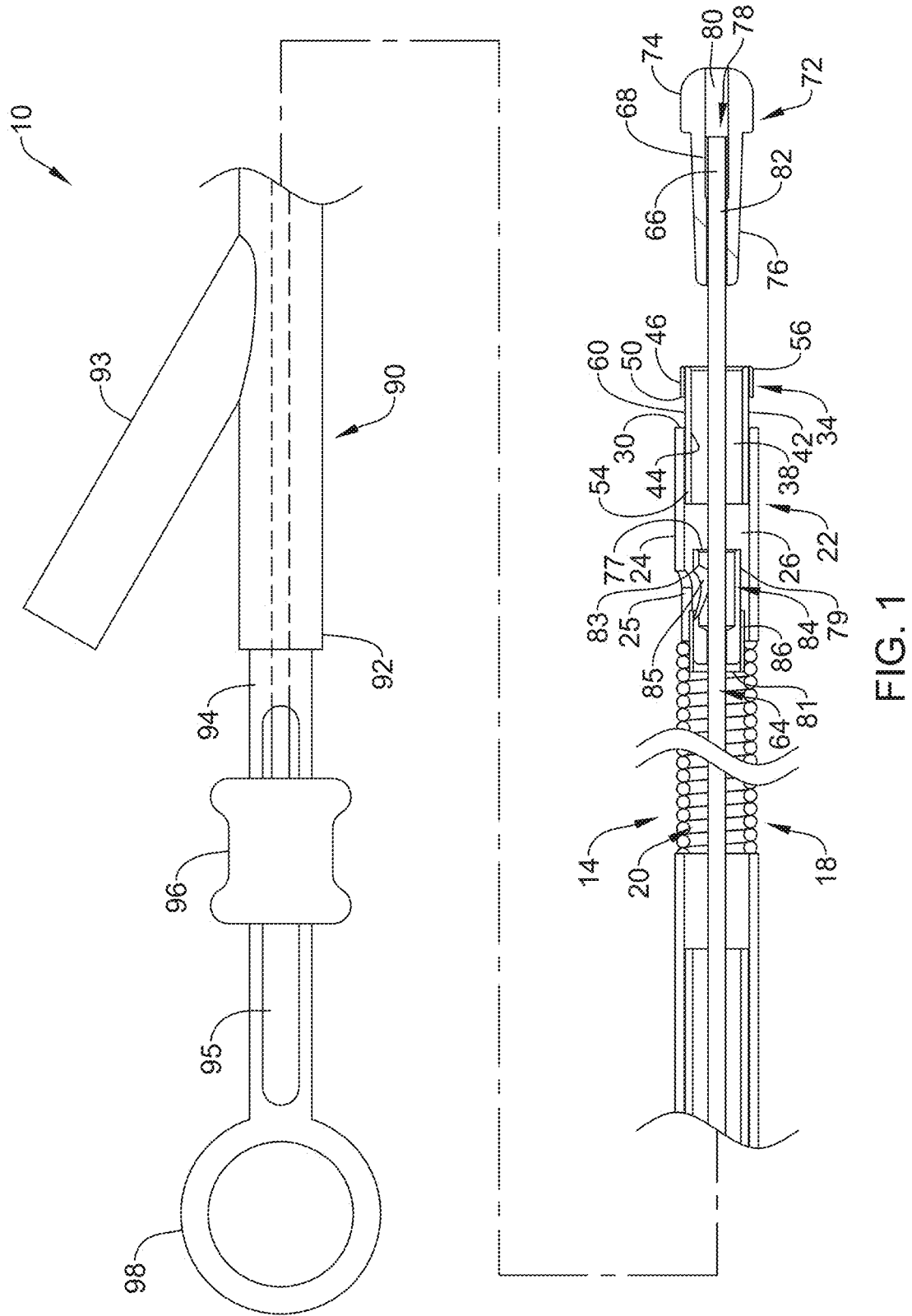
FIG. 1 is a partial cross-sectional side view of an example medical device for applying a cinch to a suture.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Medical suturing is used in a number of different interventions. Some of the interventions may include suturing at remote sites within the patient and/or otherwise at sites that may be challenging to access. When the suturing process is complete, it may be desirable to terminate the suture in a way that maintains the suture so that the suture does not easily come undone. This may include using a device such as a cinch in order to maintain the suture. Disclosed herein are medical devices that may be used to suture tissue as well as to terminate the suture. At least some of these devices utilize a cinch to maintain the suture. Some additional details of such devices are disclosed herein.

Figure 2:
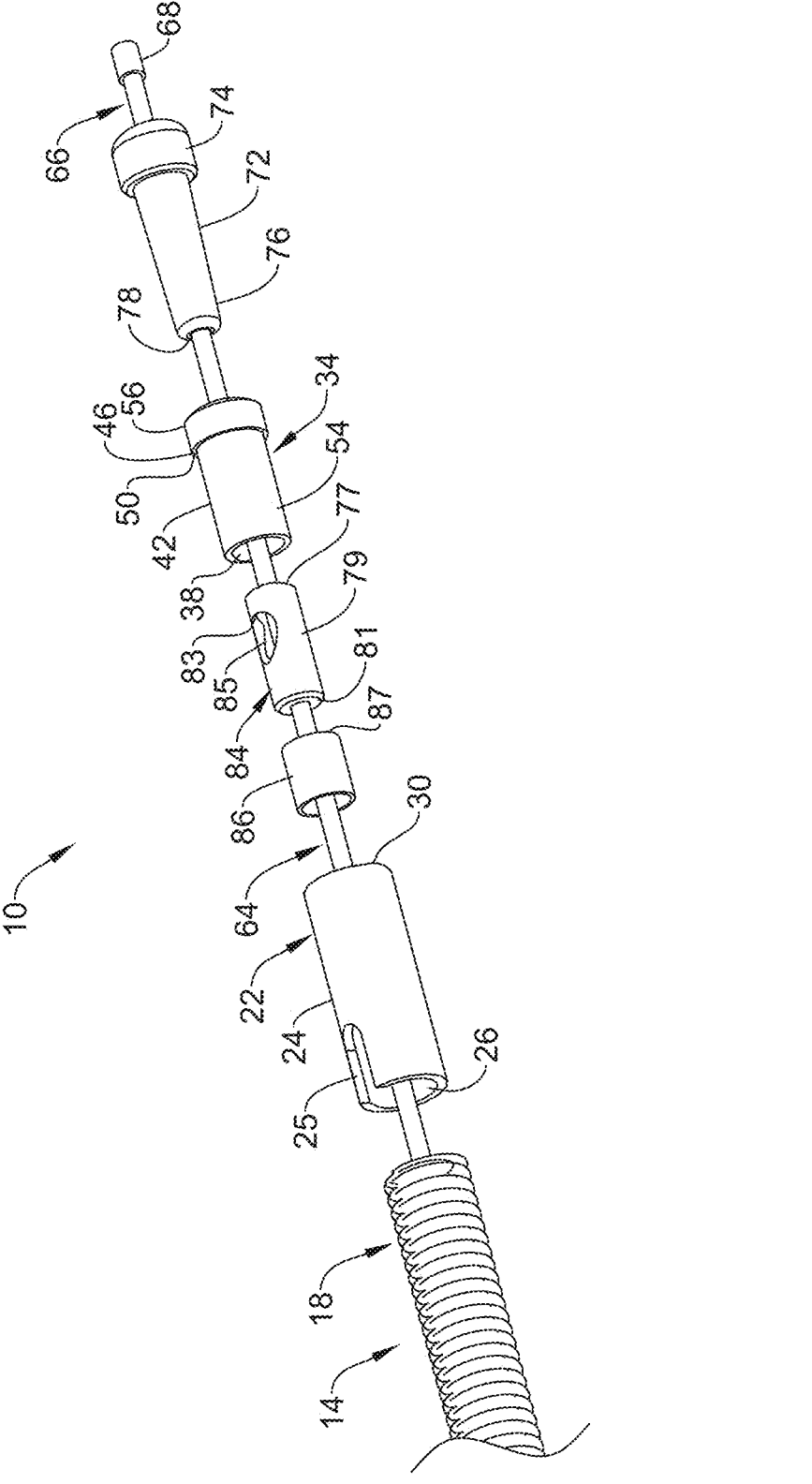
FIG. 2 is a partial exploded view of the medical device of FIG. 1.

FIG. 1 shows a partial cross-sectional side view of a medical device 10 for applying a cinch to a suture, and FIG. 2 is a partially exploded view of the medical device 10, showing some of the components of the medical device 10. The medical device 10 may include an elongated shaft 14, an outer cinch member 34, an elongated inner shaft 64, and an inner cinch member 72.

The elongated shaft 14 includes a proximal region 18 and a distal region 22. The proximal region 18 may include and/or be made of an elongated tubular member defining a lumen 20 having a lumen diameter. In the embodiment shown, the proximal region 18 is coiled tubular shaft, however, other configurations are contemplated. For example, the proximal region 18 may be a solid metallic or polymer tubular member, a tubular member including and/or made of and/or reinforced with a coil, braid and/or mesh material, or the like. Further, the proximal region 18 may include one or more slots and/or grooves and/or channels formed therein, for example, to enhance the flexibility characteristics thereof. The proximal region 18 may include or be made of one or more metals, polymers, and/or composite or layered or reinforced structures thereof, including any of those disclosed herein.

The distal region 22 may be a tubular member including tubular wall 24 defining a lumen 26 having a lumen diameter, and including a distally facing end surface 30. The distal region 22, including the lumen 26, may be configured to function as a receiver and/or "socket" for receiving and maintaining at least a portion of the outer cinch member 34 therein, as will be discussed below. In the embodiment shown, the distal region 22 is a generally solid metallic tubular member, however, other configurations are contemplated. For example, the distal region 22 may be a polymer tubular member, a tubular member including and/or made of and/or reinforced with a coil and/or braid and/or mesh material, or the like. Further, the distal region 22 may include one or more slots or grooves or channels formed therein, for example, to enhance the flexibility characteristics thereof. The distal region 22 may include or be made of one or more metals, polymers, and/or composite or layered or reinforced structures thereof, including any of those disclosed herein.

The proximal region 18 and the distal region 22 may be one integral piece, or may be separate parts connected such that the lumen 26 is in communication with the lumen 20, for example, in an end to end arrangement. Arrangements are contemplated where the lumens 20, 26 may or may not be coaxial. In some embodiments, the lumen diameters of the lumen 20 and the lumen 26 are the same or similar, while in other embodiments they may differ.

The distal region 22 may optionally include a cutout 25 that extends through the wall 24. The cutout 25 may provide access to the lumen 26 through the wall 24, for example, such that a suture may extend there through when the device 10 is used in a "side saddle" arrangement—where the suture extends from within the lumen 26 through the cutout 25, and a proximal portion of the suture extends external of the device 10 along the proximal region 18 of the shaft 14, as will be discussed in more detail below. However, as indicated, such a cutout 25 is optional. For example, it is also contemplated that the device 10 may be used with a suture in a "through-the-device" arrangement—where the suture, rather than extending externally along the proximal region 18, extends internally along and through the lumen 20 of the proximal region 18 of the device 10, as discussed in more detail herein. In such an arrangement, the cutout 25 may not be necessary.

The outer cinch member 34 may be a tubular member including an inner surface 44 defining a bore 38 extending there through, and an outer surface 42. The bore 38 may be sized and/or configured to receive and/or engage a portion of the inner cinch member 72, as discussed herein. The bore 38 may have a tapered or constant inner diameter. The outer cinch member 34 is configured and/or designed to mate with the inner cinch 72 to trap and/or wedge a portion of a suture there between. As such, the outer cinch 34, in combination with the inner cinch 72, make up the "cinch" that will be applied to the suture.

The outer cinch member 34 includes a proximal portion 54 and a distal portion 56. The proximal portion 54 includes an outer diameter and is sized and/or configured to fit within the lumen 26 of the distal region 22 of the elongated shaft 14. The outer surface 42 defines a widened diameter portion and/or shoulder 46 having a proximally facing shoulder surface 50. The widened diameter portion and/or shoulder 46 and/or the entire distal portion 56 may include an outer diameter that is larger than the inner diameter of the lumen 26, and as such may be configured such that they cannot fit into the lumen 26 of the distal region 22. In the embodiment shown, shoulder 46 is defined by a generally stepped portion having a rapid and/or stepped increase in outer diameter. However, in other embodiments, the outer surface 42 may be tapered and/or angled gradually and/or in a stepwise fashion such that the outer diameter increases in size in a distal direction in a more gradual manner, and the shoulder 46 may be more subtle. In such embodiments, the widened diameter portion and/or shoulder 46 may simply be defined by a first part along the outer surface 42 that includes an outer diameter sized such that it cannot fit into the lumen 26. Such embodiments will still include a proximally facing shoulder surface 50, in that the angle and/or taper would still provide a surface that is facing in a proximal direction in a tapered and/or angled manner.

In FIG. 1, the outer cinch member 34 has and/or is disposed in a first configuration, where the proximal portion 54 is disposed within the lumen 26 and is engaged with the distal region 22 of the elongated shaft 14 such that a gap 60 is defined between the proximally facing shoulder surface 50 and the distally facing end surface 30. For example, the outer cinch member 34 may be fixedly engaged with the distal region 22 of the elongated shaft 14 with one or more frangible bond. The frangible bond may be a connection and/or attachment between the outer cinch member 34 and the distal region 22 that is designed to temporarily and/or provisionally fixedly secure or engage the components together, and is also designed to be selectively broken and/or overcome and/or released when desired to release the fixable securement of the components such that they may be moved relative to one another. For example, the one of more frangible bonds may include a frangible weld, such as a tack weld, a frangible adhesive bond, a frangible solder bond, a frangible mechanical interlock, a frangible frictional engagement, or the like, between the outer surface 42 of the outer cinch member 34 and a surface (e.g. luminal surface of the lumen 26) of the distal region 22. These frangible bonds may be selectively broken and/or overcome and/or released, for example, by the application of a predetermined amount of relative longitudinal force applied between the outer cinch member 34 and the distal region 22. For example, the outer cinch member 34 may be releasably engaged and/or releasably coupled and/or releasably bonded and/or releasably connected and/or releasably attached with the distal region 22 when in the first configuration, such that such that the gap 60 is defined between the proximally facing shoulder surface 50 and the distally facing end surface 30. The releasable engagement and/or coupling and/or bond and/or connection and/or attachment may be selectively overcome and/or released and/or broken, for example, by the application of a predetermined amount of relative longitudinal force applied between the outer cinch member 34 and the distal region 22. The outer cinch member 34 may also include a second configuration, where the frangible bond(s) between the outer cinch member 34 and the distal region 22 is broken and/or overcome and/or released, the outer cinch member 34 has moved longitudinally relative to the distal region 22, and the gap 60 has closed. For example, the releasable engagement and/or coupling and/or bond and/or connection and/or attachment may be selectively overcome and/or released and/or broken, for example, by the application of a predetermined amount of relative longitudinal force applied between the outer cinch member 34 and the distal region 22. For example, the proximally facing shoulder surface 50 may engage the distally facing end surface 30 in the second configuration.

The elongated inner shaft 64 may be a solid wire or ribbon, or may be a generally tubular member defining a lumen along a part or the entire length thereof, or a combination of these structures. The elongated inner shaft 64 extends through and is longitudinally movable within the elongated shaft 14 from the proximal end of the device 10, distally, to the distal end of the device 10. For example, inner shaft 64 extends into and through the lumen 20 of the proximal region 18 and into and through the lumen 26 of the distal region 22. The inner shaft 64 also extends into and through and is longitudinally movable within the bore 38 of the outer cinch member 34. The elongated inner shaft 64 includes a distal end section 66 configured to engage the inner cinch member 72. For example, the distal end section 66 may include an enlarged section 68 configured to engage the inner cinch member 72 in an interference fit, as discussed in more detail herein. The enlarged section 68 may be an integral portion of the elongated inner shaft 64, or may be a separately attached component. For example, enlarged section 68 may simply be a rounded, bulbous and/or enlarged diameter portion of the inner shaft 64 itself, or may be a separately attached polymer or metallic sleeve, tube, coil, braid, or the like, to provide an enlarged diameter. In some embodiments, the enlarged section 68 may be made of and/or include a deformable material, such that when a predetermined axial compressive force is applied thereto, it may expand radially, either temporarily or permanently.

The inner cinch member 72 may be a tubular member defining a bore 78 extending there through. The bore 78 may be sized and/or configured to receive and/or engage a portion of the elongated inner shaft 64, which may extend at least partially there through. For example, the bore 78 may include distal section 80 and a proximal section 82. The distal section 80 may include an increased diameter relative to the proximal section 82, and may be sized and/or configured to receive the enlarged section 68 of the inner shaft 64 therein. In essence, the distal section 80 has an enlarged diameter that forms a pocket for the enlarged section 68 of the inner shaft 64. The proximal section 82 may include a decreased diameter relative to the distal section 80, and may be sized and/or configured to receive a portion of the shaft 64 that is proximal to the enlarged section 68. This configuration may provide an interference fit and/or engagement between the inner cinch member 72 and the inner shaft 64. For example, there is an interference fit between the proximal section 82 of the bore 38 and the enlarged section 68 of the inner shaft 64, in particular when a proximal longitudinal force and/or movement is applied to the inner shaft 64. The size difference between the proximal section 82 (which is narrower) and the enlarged section 68 (which is wider) provides resistance to the enlarged section 68 pulling through the narrower proximal section 82 of the bore 78. However, either the inner cinch member 72 and/or the enlarged section 68 of the inner shaft 64, or both, may be deformable and/or flexible, such that the application of a predetermined amount of longitudinal force allows the interference fit to be overcome, thereby allowing the enlarged section 68 to be pulled through the narrower proximal section 82 of the bore 78.

The inner cinch member 72 includes a distal portion 74 and a proximal portion 76. The proximal portion 76 includes an outer diameter and is sized and/or configured to fit within the bore 38 of the outer cinch member 34. The proximal portion 76 may have a tapered or constant outer diameter. The outer diameter and/or surface of the proximal portion 76 may be configured to engage the inner surface of the bore 38 of the outer cinch member 34 in an interference fit and/or frictional engagement to engage the inner cinch member 72 with the outer cinch member 34. The inner cinch member 72 is configured and/or designed to mate with the outer cinch member 34 to trap and/or wedge a portion of a suture there between. As such, the outer cinch 34, in combination with the inner cinch 72, make up the "cinch" that will be applied to the suture.

The distal portion 74 may include an outer diameter that is larger than the inner diameter of the bore 38, and as such may be configured such that it cannot fit into the bore 38 of the outer cinch member 34. The transition between the diameters of the distal portion 74 and a proximal portion 76 may occur rapidly, defining a generally stepped shoulder portion having a rapid and/or stepped increase in outer diameter. However, in other embodiments, the transition in diameters may be tapered and/or angled gradually and/or in a stepwise fashion such that the outer diameter increases in size in a distal direction in a more gradual manner, and a more subtle shoulder may be defined. In such embodiments, the widened diameter portion and/or shoulder may simply be defined by a first part along the inner cinch member 72 that includes an outer diameter sized such that it cannot fit into the bore 38 of the outer cinch member 34.

In at least some instances, the medical device 10 may include a suture cutting member 84. In the example depicted in FIGS. 1-2, the suture cutting member 84 may be disposed at least partially within the lumen 26 of the distal region 22 of the elongated shaft 14. The inner shaft 64 may extend through the suture cutting member 84. In general, the suture cutting member 84 may be designed to terminate and/or otherwise cut a suture used with the device 10. However, in some instances, the device 10 may include a different structural feature or component for cutting the suture and/or another device may be used in conjunction with the device 10 in order to cut the suture. Indeed, some example embodiments of the device 10 are contemplated that do not include the suture cutting member 84.

Figure 3:
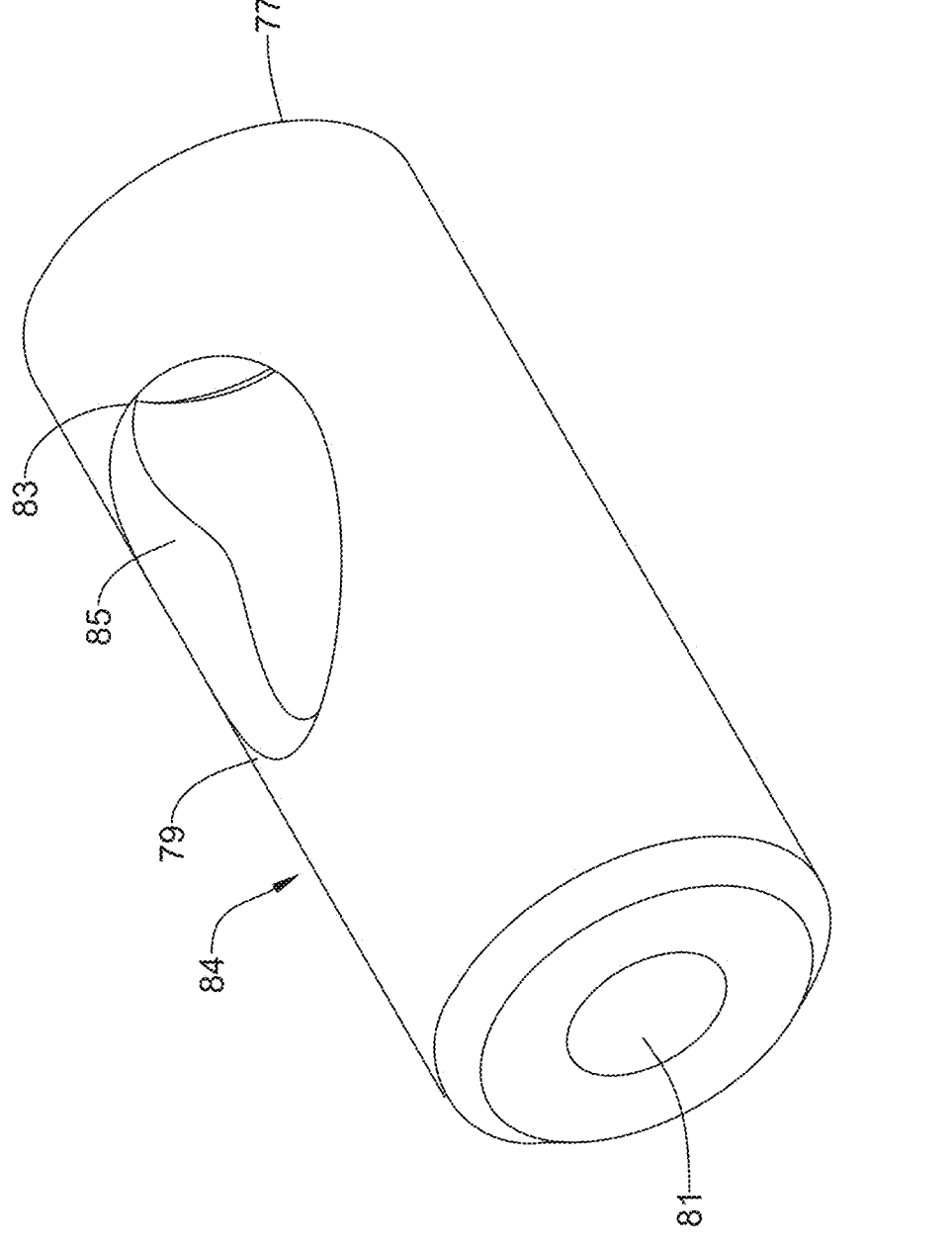
FIG. 3 is a perspective side view a cutter member of the medical device of FIG. 1.

FIG. 3 shows a perspective view of the suture cutting member 84, illustrating some of the features thereof. Here it can be seen that the suture cutting member 84 may be a generally tubular member including a wall 79 having an outer diameter and defining a lumen having a distal opening 77 and a proximal opening 81. In at least some instances, the distal opening 77 may be designed so that the inner shaft 64 can pass there through. The proximal opening 81 may be designed so that the inner shaft 64 can extend at least partially there through. However, the proximal opening 81 may be narrower than the distal opening 77. For example, the proximal opening 81 may be sized so that the enlarged section 68 of the inner shaft 64 may not be able to pass through the proximal opening 81. This may provide an engagement mechanism between the inner shaft 64 and the suture cutting member 84 such that proximal retraction of the inner shaft 64 (e.g., relative to the suture cutting member 84) may include engagement of the enlarged section 68 of the inner shaft 64 with the suture cutting member 84 (e.g., at a location adjacent to the proximal opening 81) such that further proximal movement of the inner shaft 64 may result in the suture cutting member 84 translating (e.g., proximally) within the lumen 26 of the shaft 14. This will be demonstrated further during the discussion of usage of the device 10 herein.

A cutout 85 may be formed in the wall 79. A shear edge 83 may be defined along the cutout 85. In at least some instances, the shear edge 83 may face in a generally proximal direction. The shear edge 83 may be used to cut a suture as described in more detail below.

Turning back to FIGS. 1-2, the device 10 may also include a "union" or shear member 86. The shear member 86 may be a generally tubular member that may be coupled to or otherwise secured within the shaft 14, for example within the lumen 20 of the proximal section, or the lumen 26 of the distal section, or both. The shear member 86 may be attached to an inner surface of the distal region 22 of the shaft, an inner surface of the proximal region 18 of the shaft 14, or both. In some instances, the shear member 86 may extend across the junction of the proximal region 18 and the distal region 22 of the shaft 14. Other arrangements are contemplated.

The shear member 86 may define a lumen having an inner diameter and also define a distally facing shear edge 87. In at least some instances, the shear edge 87 of the shear member 86 may be designed to work with the shear edge 83 of the suture cutting member 84 such that a suture disposed between the shear edges 87, 83 may be cut or sheared when the shear edges 87, 83 come together. In at least some embodiments, the shear member 86 is configured to receive a portion of the suture cutting member 84 therein. For example, the shear member 86 may include an inner diameter that is the same as or larger than the outer diameter of the suture cutting member 84, such that at least a portion of the suture cutting member 84 is configured to be disposed within at least a portion of the shear member 86. In at least some embodiments, it may be desirable to have a tight tolerance fit between the inner diameter of the shear member 86 and the outer diameter of the suture cutting member 84 to provide for a better suture cutting arrangement between the shear edges 87, 83.

Figure 4:
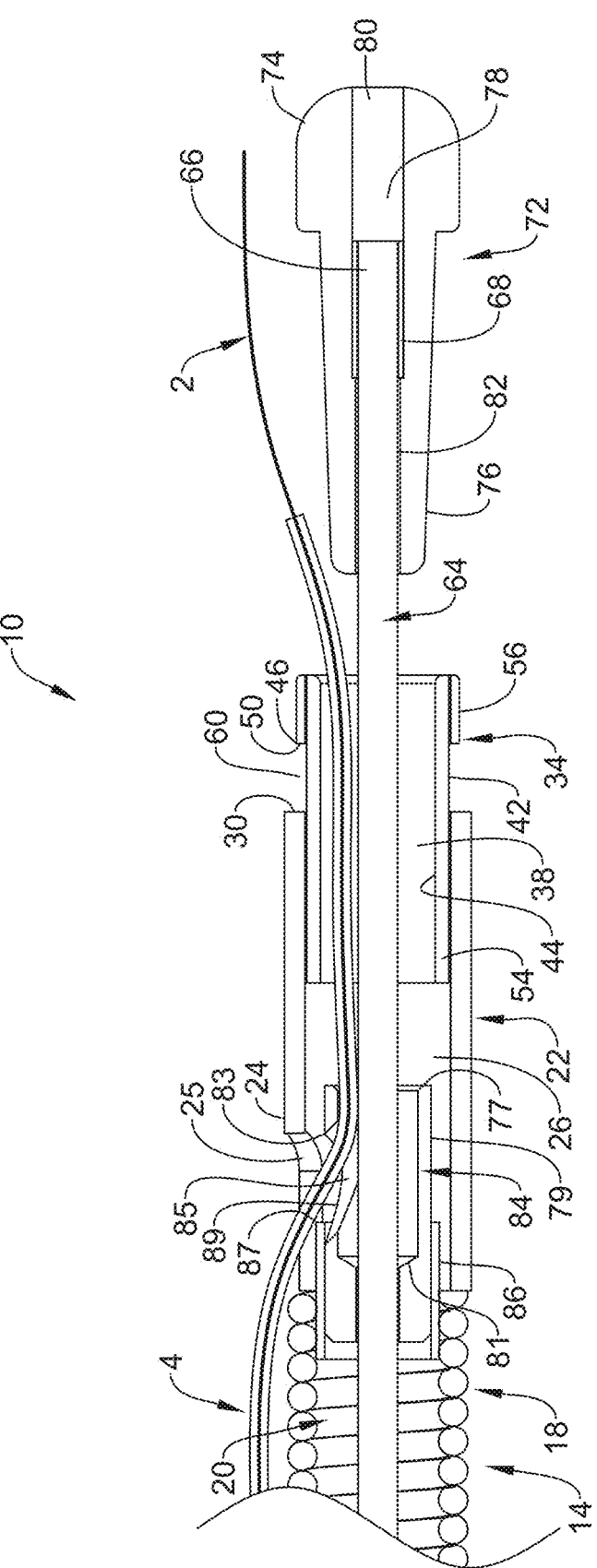
FIG. 4 is a side cross-sectional view of a portion of the medical device of FIG. 1 wherein the inner and outer cinch members are spaced longitudinally (not directly engaged), the outer cinch member is in a first configuration, the cutter is in an open configuration, and a suture guide tube and a suture are loaded through the device in a side saddle arrangement.
Figure 9:
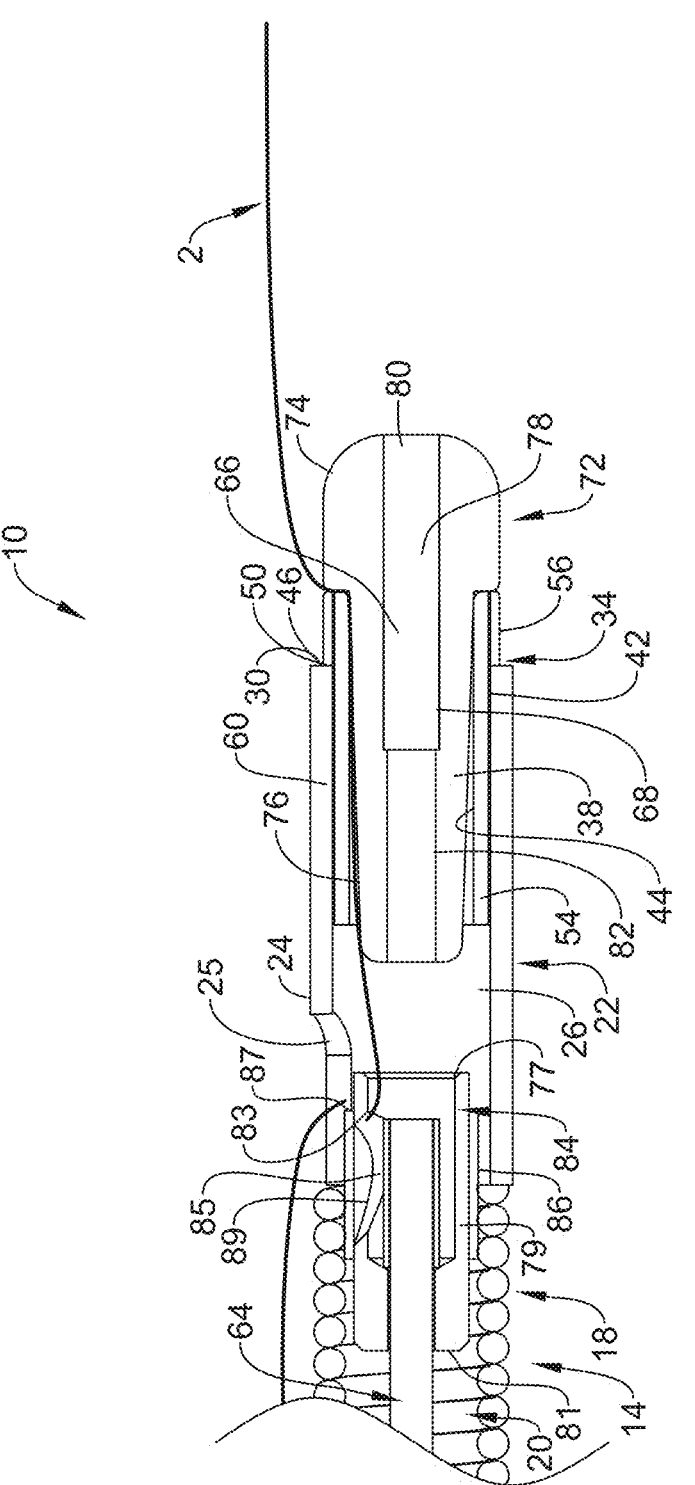
FIG. 9 is a side cross-sectional view of a portion of the medical device of FIG. 8, wherein the inner shaft has been moved further proximally and has engaged the cutter to move the cutter proximally to cut the suture.

The suture cutting member 84 may be designed to shift between a first or open configuration (e.g., as depicted in FIG. 4 and where an opening 89 is defined between the shear edge 83 of the suture cutting member 84 and the shear edge 87 of the shear member 86) and a second or closed configuration (e.g., as depicted in FIG. 9 and where the shear edge 83 of the suture cutting member 84 is brought adjacent to and/or engages the shear edge 87 of the shear member 86). In some instances, the suture cutting member 84 (e.g., a proximal portion of the suture cutting member 84) may be coupled to the shear member 86, for example with a frangible bond. For example, a proximal portion of the suture cutting member 84 may be disposed within a distal portion of the shear member 86, and the two structures may be fixedly secured to each other with a frangible bond while in the open configuration. Thus, in an original state where the frangible bond is intact, the suture cutting member 84 may be in the open configuration. Proximal retraction of the inner shaft 64 may bring the enlarged section 68 of the inner member 64 into contact with a surface of the suture cutting member 84 (e.g., adjacent to the proximal opening 81) so that further proximal retraction of the inner shaft 64 may break or sever the frangible bond and allow the suture cutting member 84 to be shifted (e.g., moved proximally) toward the closed configuration.

Turning back to FIG. 1, the medical device 10 also includes a handle and/or user interface 90 that may be designed and/or configured for user interaction to provide relative movement between the elongated shaft 14 and the inner shaft 64. Any of a wide variety of configurations of the user interface 90 are contemplated that may achieve this purpose. In the embodiment shown in FIG. 1, the user interface 90 incudes a distal portion 92, a proximal portion 94, and a slider portion 96 that is disposed about and/or along the proximal portion 94. The distal portion 92 is connected to the proximal end of the elongated shaft 14, and the proximal portion 94 is connected to and extends proximally from the distal portion 92. The slider portion 96 is connected to the proximal end of the inner shaft 64. The slider portion 96 is disposed on and longitudinally movable and/or slidable over and/or along the proximal portion 94. As such, the user interface may provide for longitudinal movement of the inner shaft 64 relative to the elongate shaft 14 by actuation of the slider 96 relative to the proximal portion 94. In some instances, the slider portion 96 may be designed to slide along a groove or slot 95 formed in the proximal portion 94. In other instances, the slider portion 96 may be replaced by one or more finger loops (not shown) designed to slide along the proximal portion 94. The finger loops may be designed to accommodate the fingers of a user (e.g., an index finger, a middle finger, combinations thereof, or other fingers) so that a user can slide the finger loops along the proximal portion 96 in order to shift the inner shaft 64 relative to the elongated shaft 14.

The proximal end of the proximal portion 94 may be configured for user engagement, and as such, may include a structure or a shape that may enhance user engagement, grip and/or comfort. For example, the proximal end of the proximal portion 94 may include a loop 98, such as a thumb loop or the like. The slider portion 96 may also be configured for user engagement, and as such may also include a structure or shape to enhance user engagement, grip and/or comfort. For example, the slider portion 96 may include a spool like configuration including an annular groove which may be configured to be engaged by one or more fingers of user. For example, a user may engage the user interface 90 by inserting a thumb into the thumb loop 98, and engaging the slider portion 96 with an index and middle finger (e.g., with the fingers disposed in the annular groove of the slider portion 96).

The user interface 90 may include a number of additional features. For example, a spool stop (not shown) may be disposed along the channel 95, which may prevent undesired movement of the spool member 96 (e.g., during shipping and/or storage). In addition or in the alternative, the user interface 90 may include one or more stops, locks, spring members, detents, indexing, markings or the like for visualizing, controlling and/or limiting longitudinal movement of the spool member 96.

The user interface 90 may also optionally include a suture exit port 93 disposed thereon, and including a lumen in communication with the lumen 20 of the proximal portion 18. For example, as discussed herein, it is contemplated that the device 10 may be used with a suture in a "through-the-device" arrangement—where the suture, rather than extending externally along the proximal region 18, extends internally along and through the lumen 20 of the proximal region 18 of the device 10. In such an arrangement, the suture will need to exit the device 10 near the proximal end. The suture exit port 93 may be used to provide this. The suture exit port 93 may be generally configured as a Y-adapter that provides proximal access to the lumen 20. The user interface 90 as described herein may be included and/or used with any of the various embodiments of medical devices disclosed herein.

FIGS. 4-10 may be used to illustrate and describe an example method of using the device 10. For example, FIG. 4 shows the medical device in an initial arrangement and ready for use. The inner cinch member 72 and the outer cinch member 34 are spaced longitudinally (and not directly engaged with each other and/or cinched onto the suture). The outer cinch 34 is in a first configuration, where the proximal portion 54 of the outer cinch member 34 is be disposed within the lumen 26 and may be engaged with the distal region 22 of the elongate shaft 14 with one or more frangible bond. A gap 60 is defined between the proximally facing shoulder surface 50 of the outer cinch member 34 and the distally facing end surface 30 of the distal region 22 of the shaft 14. In essence, the distal region 22 is acting as a "socket" for securely holding (e.g. frangibly bonded to) the outer cinch member 34 during delivery, until it is desirable to release it. The inner cinch member 72 is mounted on the elongate shaft 64, and the interference fit provided by the enlarged section 68 maintains the inner cinch member 72 thereon during delivery, until it is desirable to release it. Also, the suture cutting member 84, if present, is in the open configuration, where an opening 89 is defined between the shear edge 83 of the suture cutting member 84 and the shear edge 87 of the shear member 86. Further, the suture cutting member 84 may be engaged with the shear member 86 with one or more frangible bond, to maintain the suture cutting member 84 in the open configuration until it is desirable to close it and cut the suture. At this stage, the device 10 is ready to be loaded with a suture and be used to apply a cinch to the suture. For example, following a suturing procedure the open and/or free and/or proximal end of the suture 2 may be loaded into and/or through the device 10. The proximal end of the suture may be fed into the distal end of the device 10 and along the appropriate pathway through the device 10. This may be done with or without using a tool or guide, such as a tubular guide, wire, loop, needle, or the like.

Figure 5:
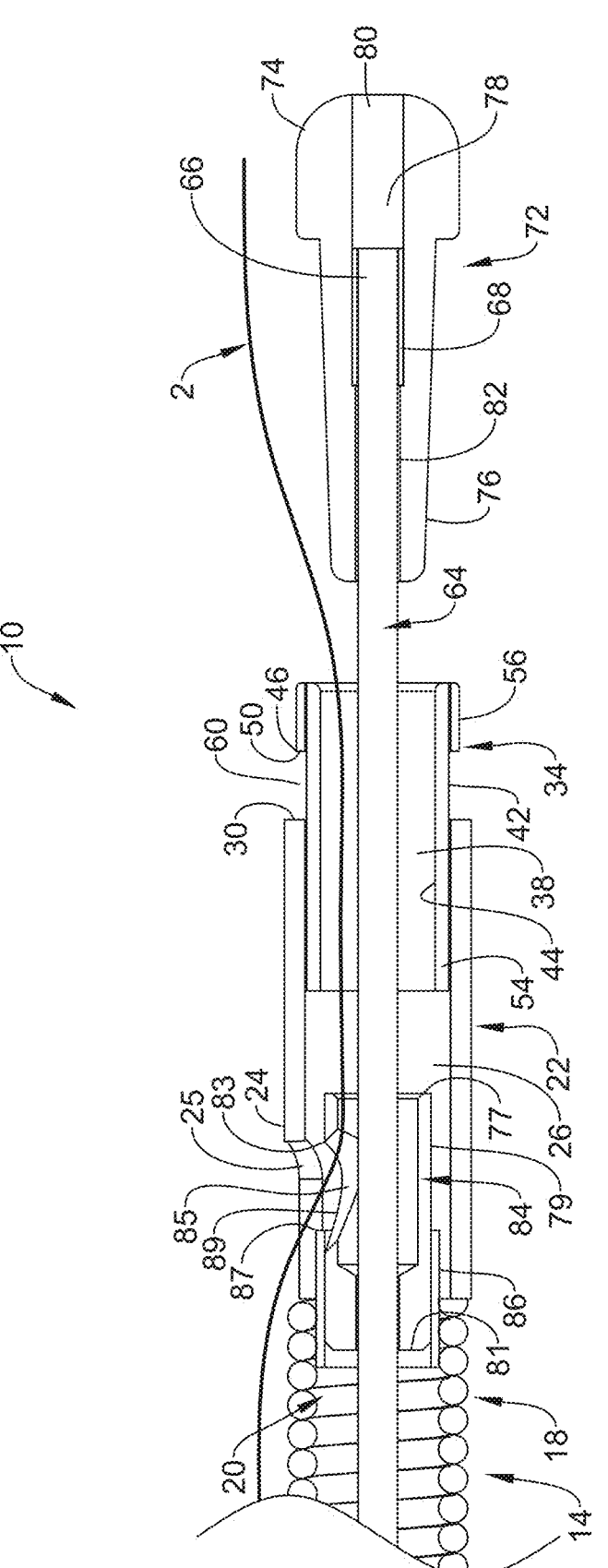
FIG. 5 is a side cross-sectional view of a portion of the medical device as shown in FIG. 4, with the suture guide tube removed.

FIG. 4 shows an example device and/or mechanism for loading the suture 2 through the medical device 10. A suture guide tube 4 may be inserted in the desired pathway for the suture 2 to extend through the device 10. In this example, the suture 2 will be loaded in a "side saddle" arrangement—where the suture 2 is loaded into the distal region of the device 10, and then extends from within the device 10 through the cutout 25, and extends external of the device 10 along the proximal region 18 of the shaft 14. For example, the suture guide tube 4 may be disposed such that it extends externally alongside the medical device 10 from the proximal end of the device 10 (e.g. adjacent the user interface 90) to the distal region 22, and then may be inserted along an appropriate pathway through the device 10. For example, as shown, the suture guide tube 4 may be inserted through the cutout 25 in the distal region 22, through the cutout 85 of the suture cutting member 84 (e.g. through the opening 89), through the lumen of the suture cutting member 84 into and through the lumen 26 of the distal region 22, into and through the bore 38 of the outer cinch member 34, and out between the outer and inner cinch members 34 and 72. The suture 2 may be fed back through the suture guide tube 4 such that is follows the same general pathway back through the suture guide tube 4 and/or device 10. The suture guide tube 4 may be used to help guide and/or load the suture 2 through the device 10 and may help protect the suture from damage, for example, from the cutter member 84 during loading of the suture. The suture guide tube 4 may be similarly used with used with any of the embodiments of medical devices disclosed herein. The suture guide tube 4 may be removed as shown in FIG. 5. The device 10 may be advanced over the suture 2 down to the suturing/defect site where it is desirable to apply a cinch to the suture 2. When doing so, the suture 2 remains inserted in the pathway through the device 10.

Figure 6:
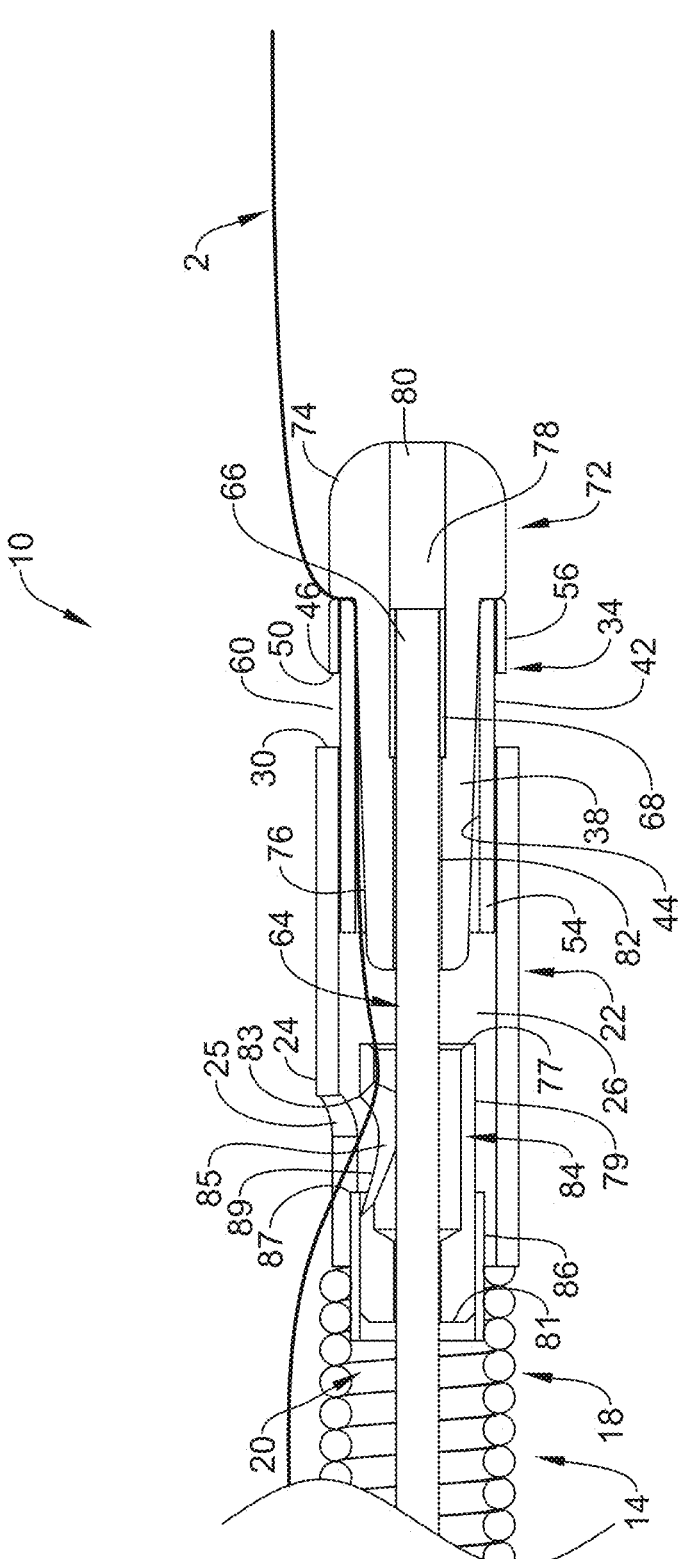

Once the device 10 is advanced to the desired position for the application of the cinch 34/72 to the suture 2, a user may apply appropriate and/or desired amount of tension to the suture 2, and apply the cinch to the suture 2 using the device 10. For example, using the user interface 90, the inner shaft 64 may be proximally retraced relative to the outer shaft 14. As shown in FIG. 6, when doing so, the inner shaft 64 may move or otherwise proximally shift the inner cinch member 72 into engagement with the outer cinch member 34, thereby trapping a portion of the suture 2 there between. The inner cinch member 72 and outer cinch members 34 are, once appropriately engaged on the suture 2, in combination, the "cinch" applied to the suture 2. This may be described as being a first stage of proximal longitudinal movement of the elongated inner shaft 64—which may apply the cinch to the suture.

Figure 7:
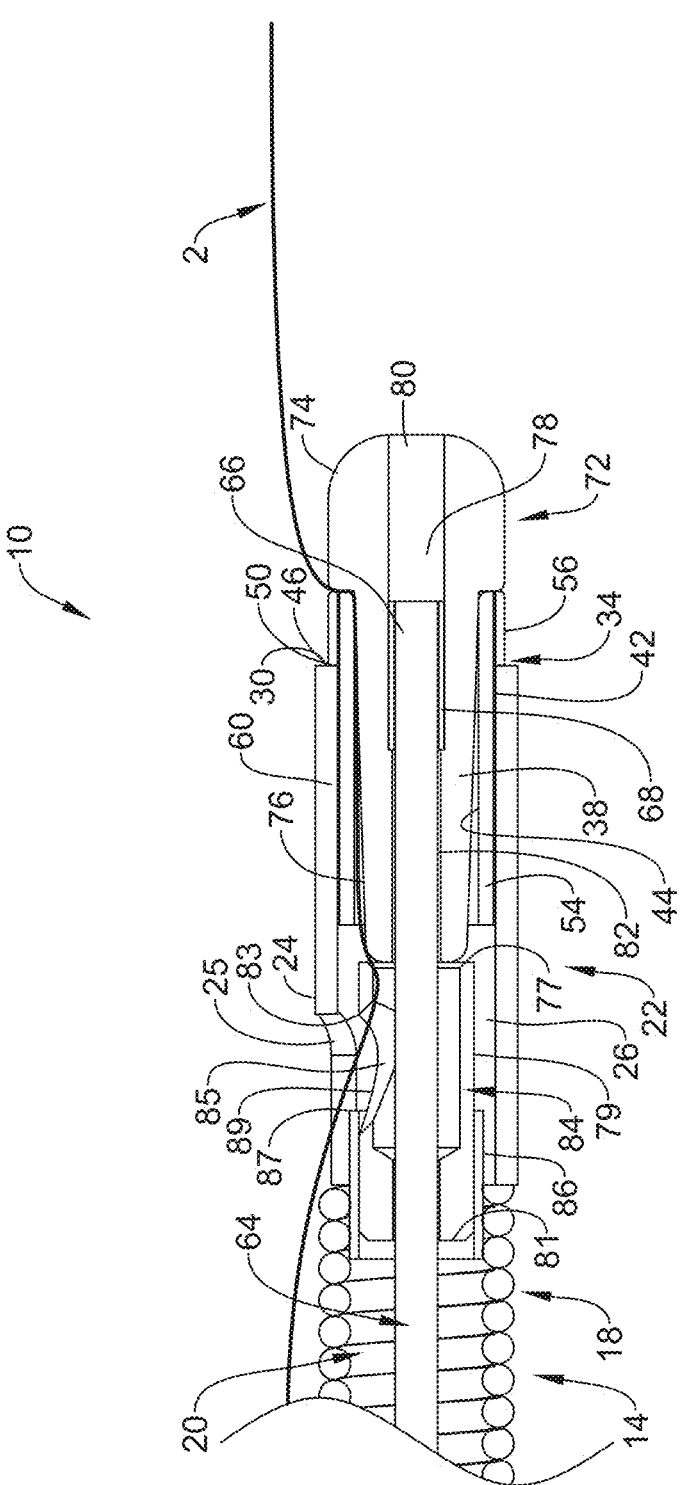
FIG. 7 is a side cross-sectional view of a portion of the medical device of FIG. 6, wherein the inner shaft has been moved further proximally, and the outer cinch member is in a second configuration.

Further proximal movement of the inner shaft 64 may shift the outer cinch member 34 from a first configuration (e.g., as shown in FIG. 5-6) toward a second configuration where the frangible bond between the outer cinch member 34 and the distal region 22 of the shaft 14 is broken and/or released, and the proximally facing shoulder surface 50 engages the distally facing end surface 30 of the elongated shaft 14 as shown in FIG. 7. This movement of the inner shaft 64 may be described as moving the inner shaft 64 proximally through a second stage of proximal longitudinal movement to shift the outer cinch member 34 toward the second configuration where the frangible bond between the outer cinch member 34 and the distal region 22 of the shaft 14 is broken and/or released. This releases the outer cinch member 34 from fixed engagement with the shaft 14, thereby allowing the cinch to be released. Additionally engaging the proximally facing shoulder 50 of the outer cinch member 34 with the distally facing end surface 30 of the distal region 22 of the elongated shaft 14 may act as a "stop" of sorts, to allow for the next stage of movement to disengage the inner cinch member 72 from the inner shaft 64.

Figure 8:
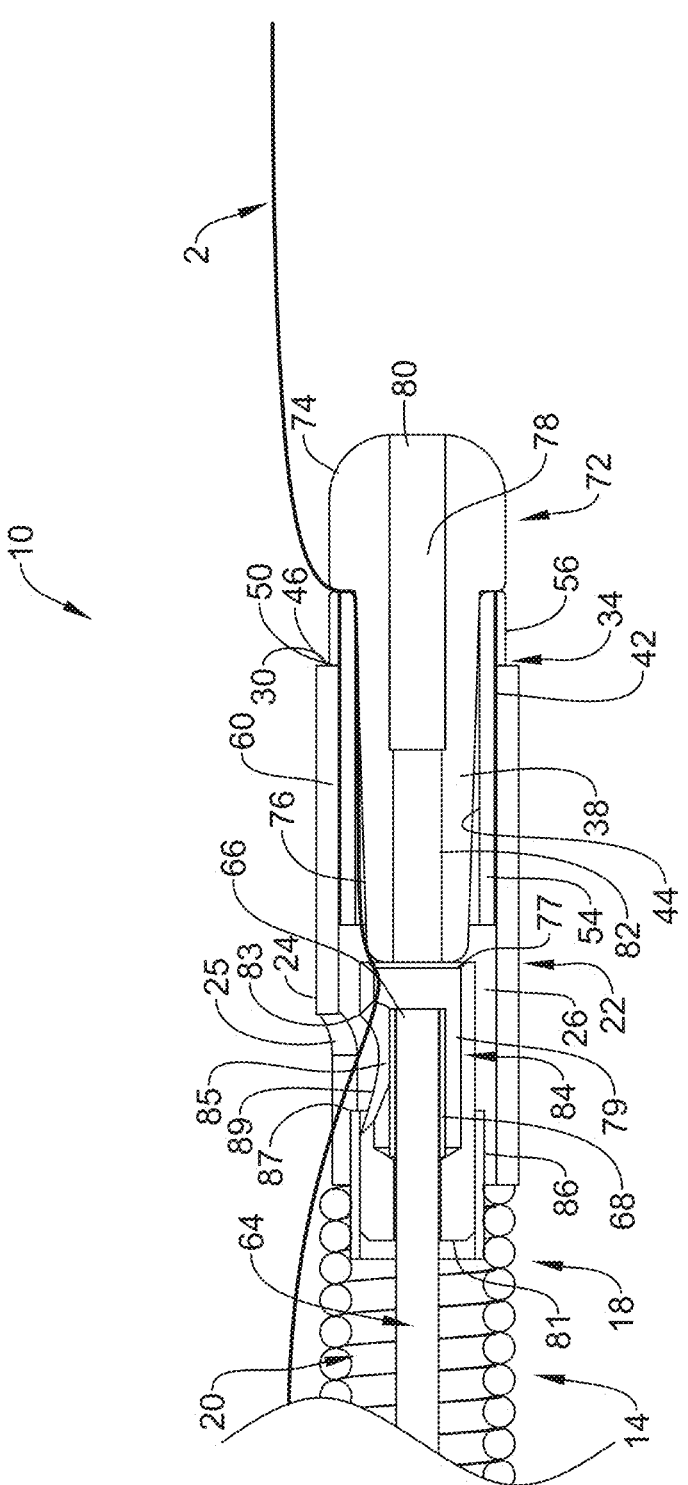
FIG. 8 is a side cross-sectional view of a portion of the medical device of FIG. 7, wherein the inner shaft has been moved further proximally is disengaged from the outer cinch member, and has engaged the cutter.

The inner shaft 64 may be designed to move through a third stage of proximal movement where the inner shaft 64 disengages from the inner cinch member 72 as shown in FIG. 8. Further, the inner shaft 64 may be designed such that a fourth stage of proximal movement of the inner shaft 64 engages the inner shaft 64 with the suture cutting member 84. When doing so, the inner shaft 64 may shift the suture cutting member 84 from the open configuration to the closed configuration and cuts the suture 2 as shown in FIG. 9. For example, moving the inner shaft 64 through the fourth stage of proximal movement may break and/or release the frangible bond between the suture cutting member 84 and the shear member 86 so that the suture cutting member 84 can shift toward the closed configuration to cut the suture.

Figure 10:
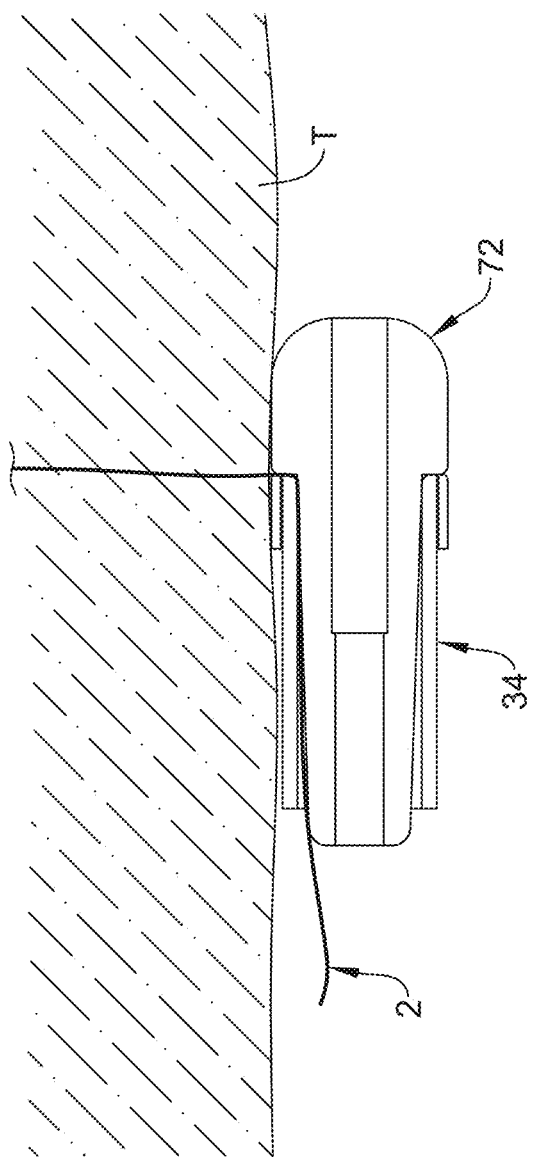

The cinch (e.g., which may be defined as or otherwise include the inner cinch member 72 and the outer cinch member 34) is applied to or otherwise holds the suture 2 in a cinched arrangement. Due to frangible bonds being broken and/or released, and the suture 2 being cut, the cinch may then be disengaged from the shaft 14 and can remain in the anatomy to terminate and/or anchor a suture that extends through tissue T as depicted in FIG. 10.

Figure 11:
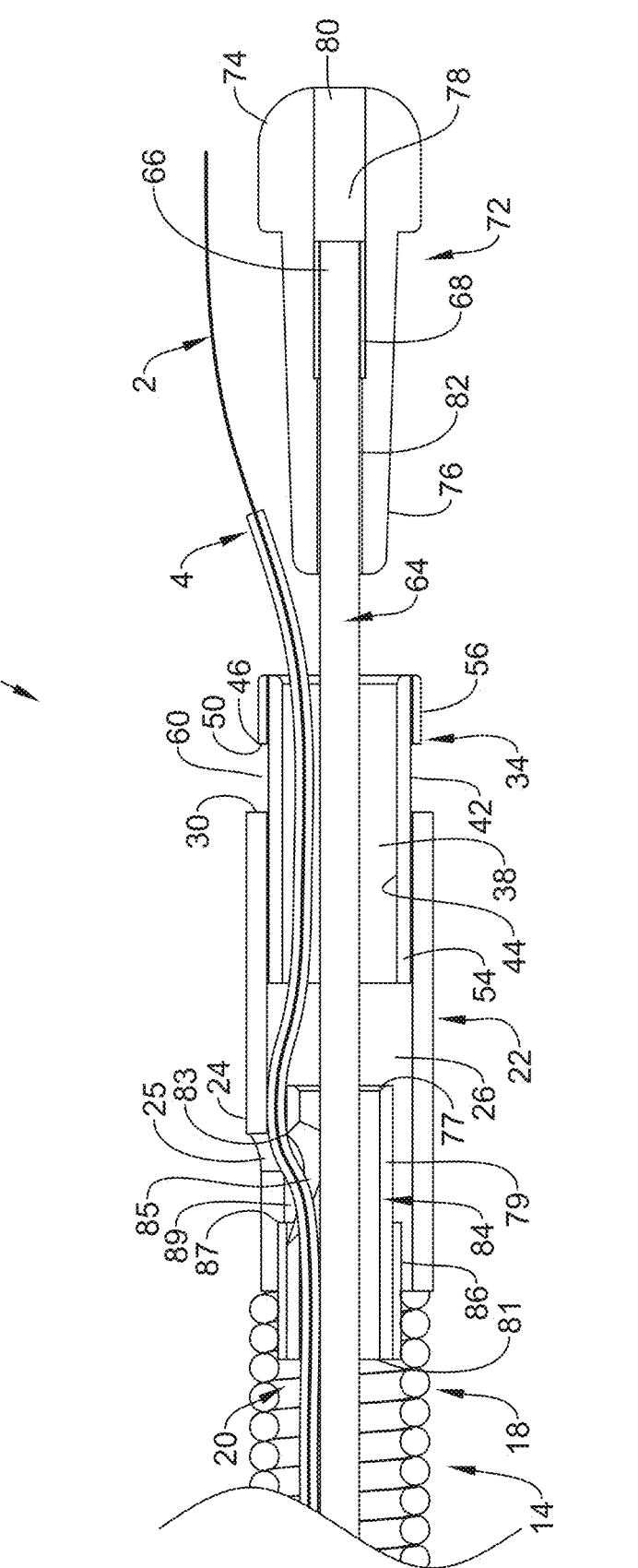
FIG. 11 is a side cross-sectional view of a portion of the medical device of FIG. 1 wherein the inner and outer cinch members are spaced longitudinally (not directly engaged), the outer cinch member is in a first configuration, the cutter is in an open configuration, and a suture guide tube and a suture are loaded through the device in a through-the-device arrangement.
Figure 12:
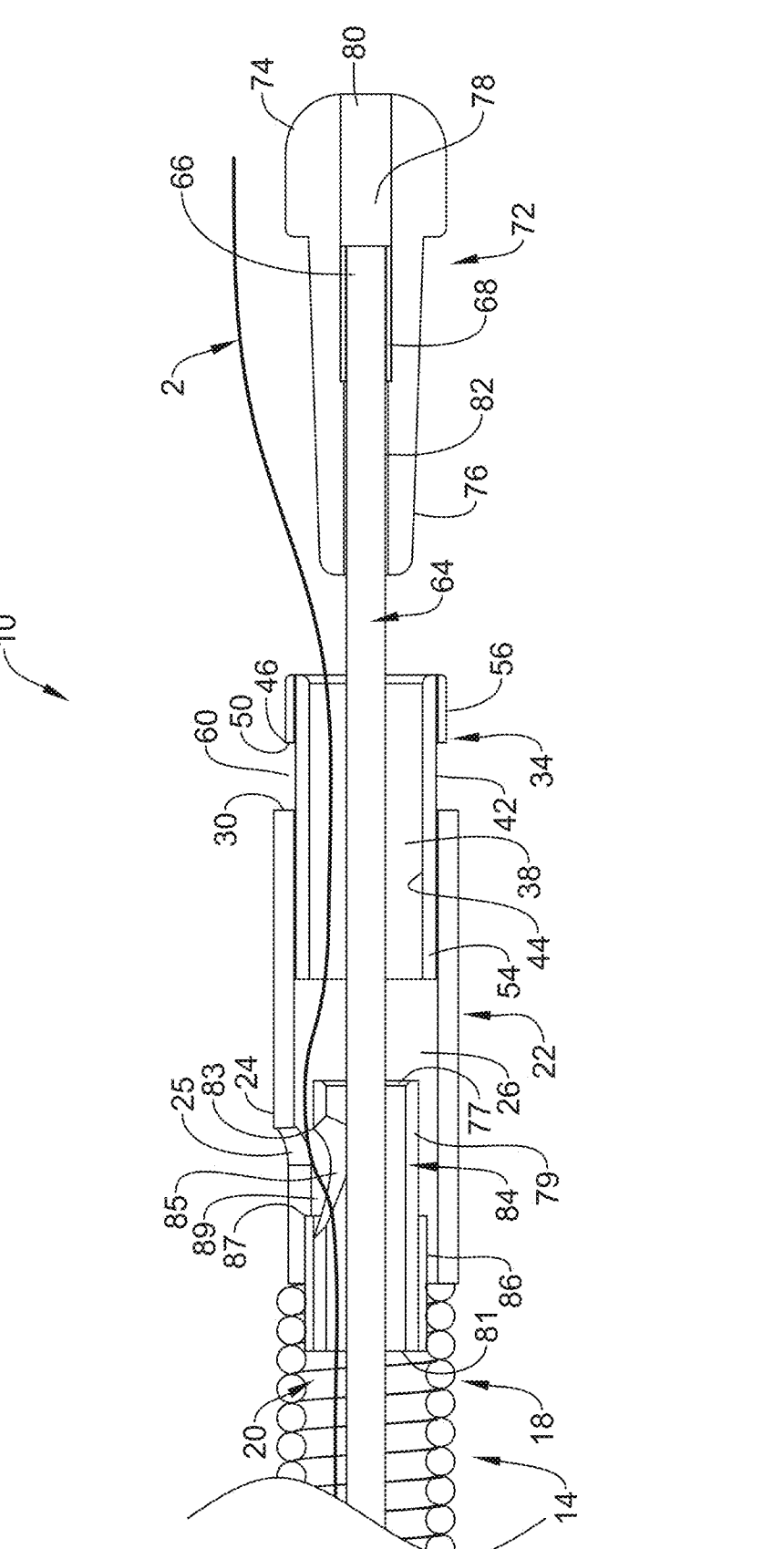
FIG. 12 is a side cross-sectional view of a portion of the medical device as shown in FIG. 11, with the suture guide tube removed.

FIGS. 11 and 12 show an alternative use and/or configuration of the device 10 relative to the suture 2 where the suture 2 is arranged in a "through the device" configuration.

For example, FIG. 11 shows the guide tube 4 being used to feed the suture 2 through the proximal portion 18 of the shaft 14 (rather than external), through the proximal portion of the suture cutting member 84, out through the cutout 85 of the suture cutting member 84, along the outside of the distal portion of the suture cutting member 84, within and through the lumen 26, into and through the lumen 38, out the distal opening of the outer cinch member 34 (e.g., between the outer cinch member 34 and the inner cinch member 72). FIG. 12 shows the guide tube 4 removed, and suture 2 remains as "through the device". At this point, use of the device 10 may be substantially the same as use described above with reference to FIGS. 4-10. For example, the device 10 may be fed over the suture 2 (which may also include tensioning the suture 2), the inner shaft 64 may be proximally retracted to engage the inner cinch member 72 with the outer cinch member 34 and apply the cinch to the suture 2. This may include moving the inner shaft 64 through a first stage and/or a second stage of longitudinal movement. Additional longitudinal movement of the inner shaft 64 (e.g., through the third and/or fourth stage) may cut the suture 2 and disengage the cinch from the device.

Figure 13:
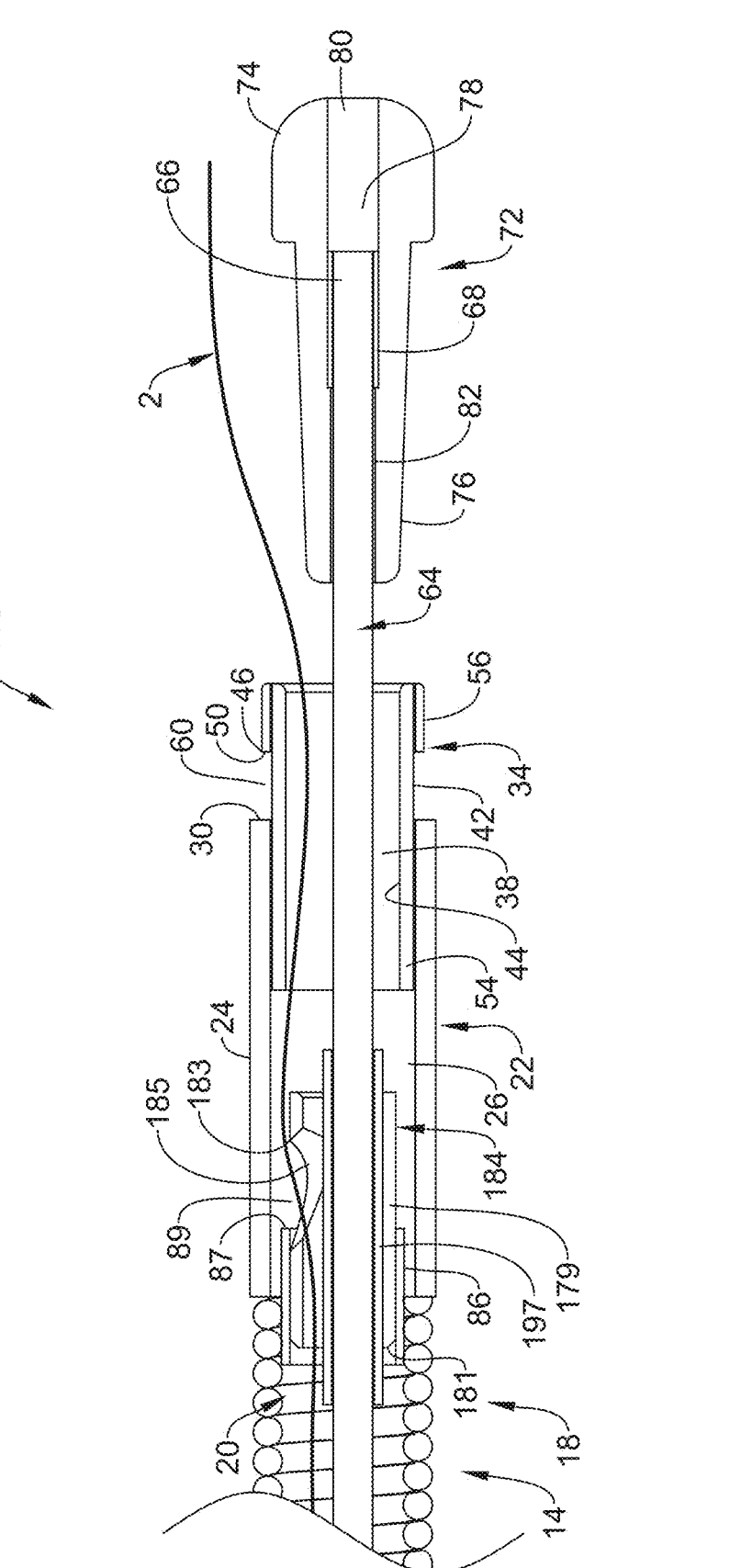
FIG. 13 is a side cross-sectional view of a portion of another embodiment of a medical device for applying a cinch to a suture including an alternative cutter configuration and showing a suture extending there through in a through-the-device configuration.
Figure 14:
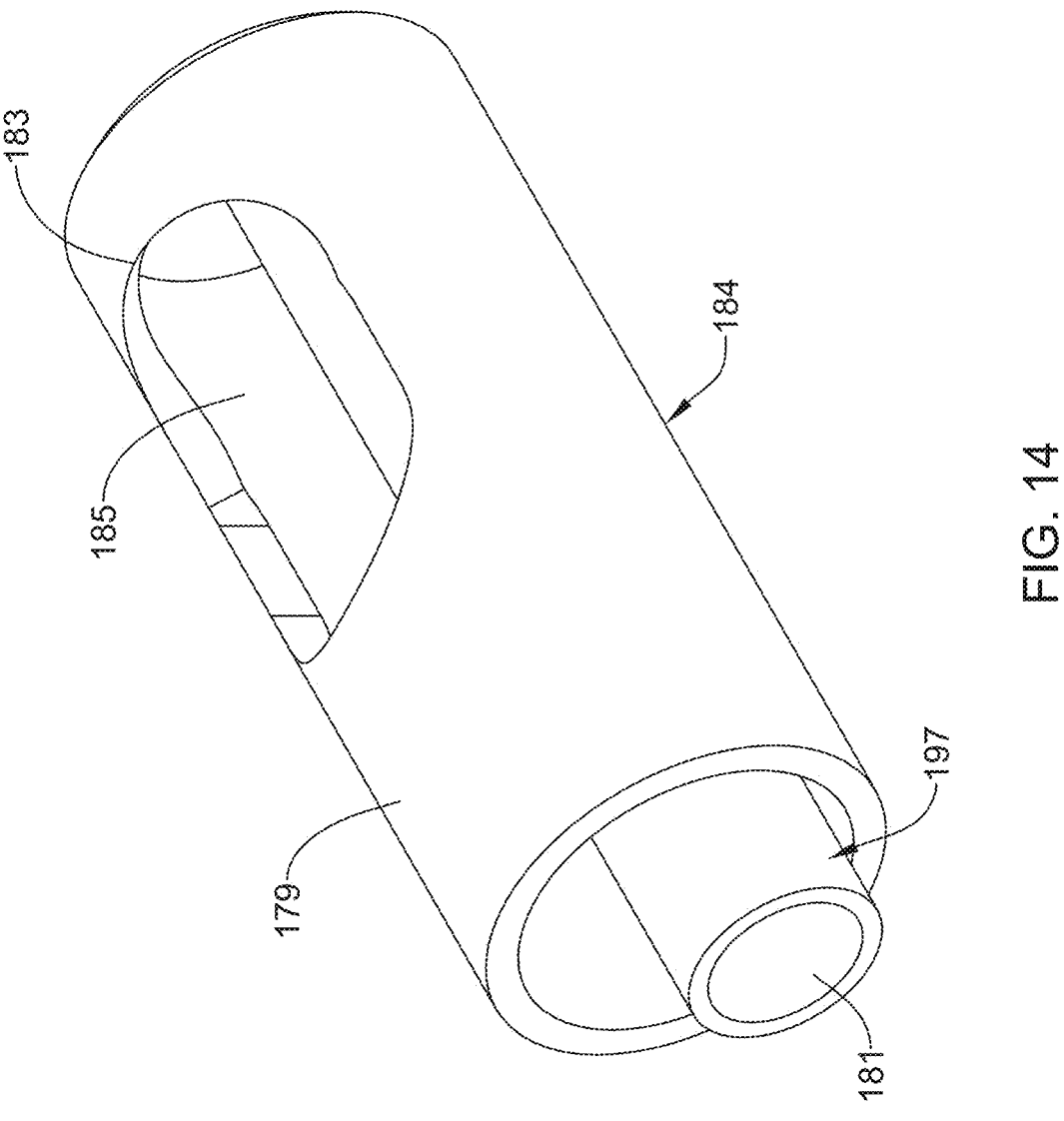
FIG. 14 is a perspective side view of the cutter member of the medical device of FIG. 13.

FIG. 13 illustrates another example medical device 110 that may be similar in form and function to the other devices described therein, wherein like names and/or reference numbers indicate the same or similar structure and/or function as described elsewhere herein. While other components of the device/assembly remain largely the same, in this example, the medical device 110 may include a suture cutting member 184, shown in FIG. 14, that includes an inner tube 197 and outer tube 179 attached to the inner tube 197. In at least some instances, the inner tube 197 is attached in a manner that is non-coaxial or could be described as being off axis. The suture cutting member 184 may include a tube wall 179. A cutout 185 may be formed in the tube wall 179 that includes or otherwise defines a shear edge 183. Cutout 185 and shear edge 183 are similar in structure and function to cutout 85 and shear edge 83 as discussed herein (e.g. the suture cutting member 184 may interact with the shear member 86 to cut the suture 2).

As such, use of the device 110 may be similar to that of other embodiments of devices described herein. For example, the device 110 may start in a first configuration, where the proximal portion 54 of the outer cinch member 34 is disposed within the lumen 26 and is engaged with the distal region 22 of the elongated shaft 14 such that a gap 60 is defined between the proximally facing shoulder surface 50 and the distally facing end surface 30. The inner shaft 64 may go through the first, second, third, and fourth stages of proximal movement, as described herein. When doing so, the cinch (e.g., including the outer cinch member 34 and the inner cinch member 72) may be applied to the suture 2, the gap 60 between the proximally facing shoulder 50 and the distal end surface 30 may close into a second configuration, the suture cutting member 184 may shift from the open to the closed configuration, to cut the suture 2, and the cinch (e.g., including the outer cinch member 34 and the inner cinch member 72) may be released.

Figure 15:
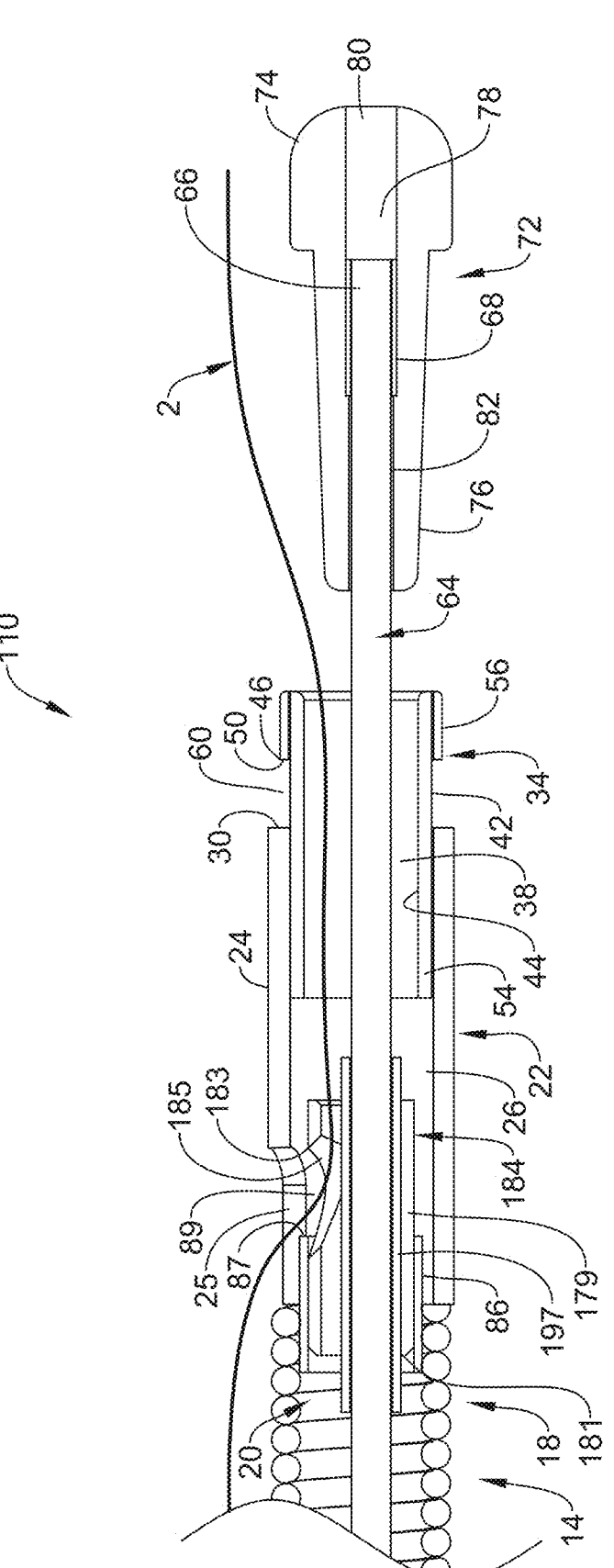
FIG. 15 is a side cross-sectional view of a portion of another embodiment of a medical device for applying a cinch to a suture similar to that shown in FIG. 13 showing a suture extending there through in a side saddle configuration.

While FIG. 13 depicts the suture 2 being arranged in a "through the device" configuration, other configurations are contemplated including a "side saddle" configuration as shown in FIG. 15. As shown in FIG. 15, when doing so, the wall of the distal region 22 of the shaft 14 may include a cutout 25 through which the suture 2 can be passed (e.g., similar to the cutout 25 as shown in FIG. 1).

Figure 16:
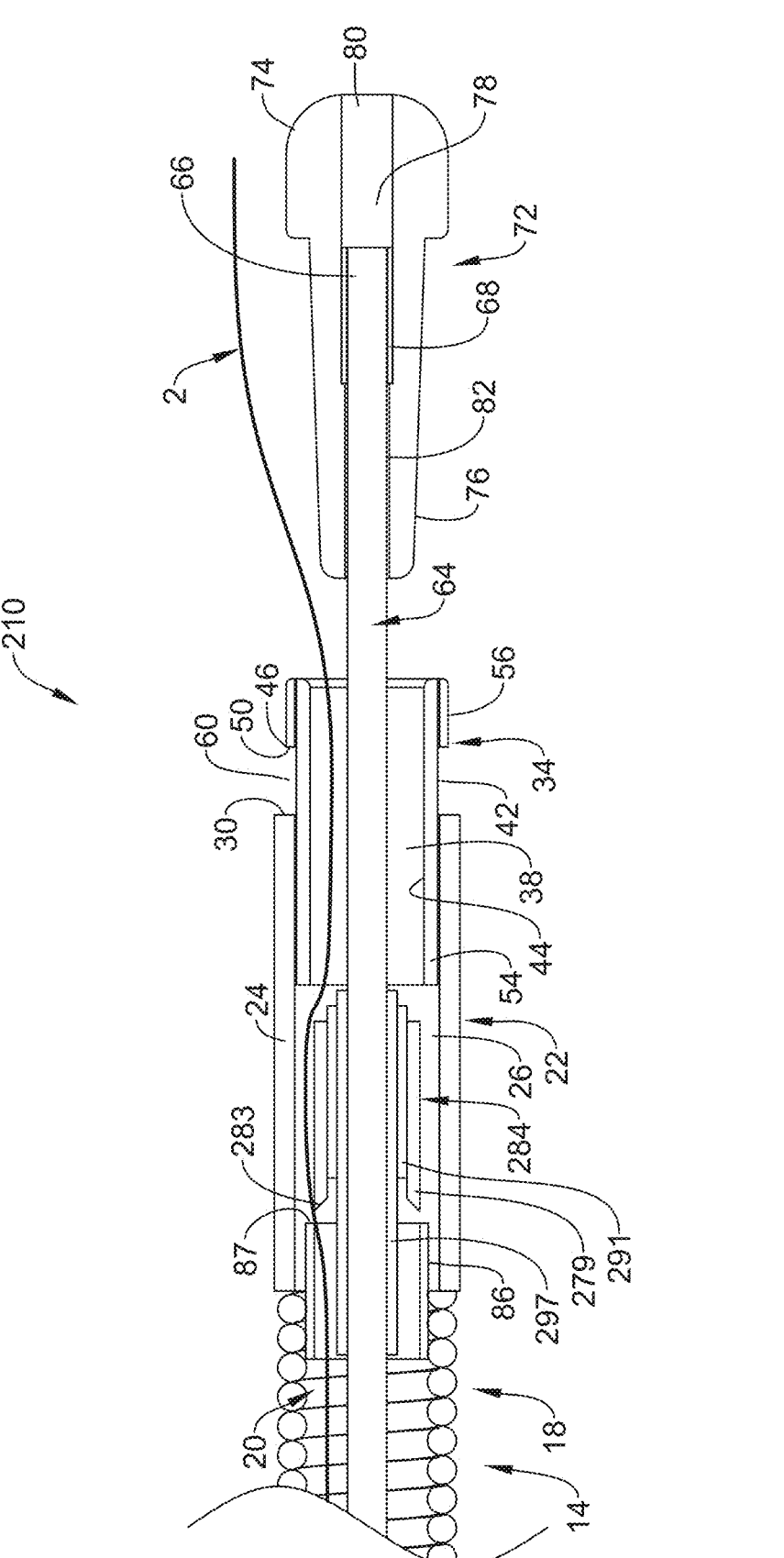
FIG. 16 is a side cross-sectional view of a portion of another embodiment of a medical device for applying a cinch to a suture including an alternative cutter configuration and showing a suture extending there through in a through-the-device configuration.

FIG. 16 depicts another example medical device 210 that may be similar in form and function to the other devices described therein, wherein like names and/or reference numbers indicate the same or similar structure and/or function as described elsewhere herein. While other components of the device/assembly remain largely the same, this embodiment includes an alternative suture cutting member 284 having a different configuration for the cutter member 284. In this example, the suture cutting member 284 may include an inner tube 297, an intermediate tube 291, and outer tube 279. As shown, the tubes 297, 291, and 279 may be arranged and/or affixed to one another on axis (e.g., the tubes 297, 291, and 279 may be coaxial). However, other arrangements are contemplated. The outer tube 279 defines a shear edge 283 on the proximal end thereof. Shear edge 283 may be similar in function to shear edge 83 as discussed herein, in that it interacts in a similar manner with the shear edge 87 of the shear member 86 to shear and/or cut the suture. The inner tube 297 receives the inner shaft 64 in the lumen there through, and an outer portion thereof may be releasably engaged/secured with the shear member 86, for example, with a frangible bond. An opening may be defined between the shear edge 283 and the shear edge 87 of the shear member 86. The intermediate tube 291 may act as a spacer between the inner and outer tubes 297, 291. Proximal retraction of the inner shaft 64 causes the distal portion 68 of the inner shaft 62 to engage the inner tube 297 and release and/or break the frangible bond. Further proximal retraction of the inner shaft 64 may bring together the shear edge 283 and shear edge 87, shifting them from an open to a closed configuration, and which engage to shear/cut the suture 2.

As such, use of the device 210 may be similar to that of other embodiments of devices described herein. For example, the device 210 may start in a first configuration, where the proximal portion 54 of the outer cinch member 34 is disposed within the lumen 26 and is engaged with the distal region 22 of the elongated shaft 14 such that a gap 60 is defined between the proximally facing shoulder surface 50 and the distally facing end surface 30. The inner shaft 64 may go through the first, second, third, and fourth stages of proximal movement, as described herein. When doing so, the cinch (e.g., including the outer cinch member 34 and the inner cinch member 72) may be applied to the suture 2, the gap 60 between the proximally facing shoulder 50 and the distal end surface 30 may close into a second configuration, the suture cutting member 284 may shift from the open to the closed configuration, to cut the suture 2, and the cinch (e.g., including the outer cinch member 34 and the inner cinch member 72) may be released.

While FIG. 16 depicts the suture 2 being arranged in a "through the device" configuration, other configurations are contemplated including a "side saddle" configuration. When doing so, the wall of the distal region 22 of the shaft 14 may include a cutout (e.g., similar to the cutout 25 as shown in FIG. 1) through which the suture 2 can be passed.

Figure 17:
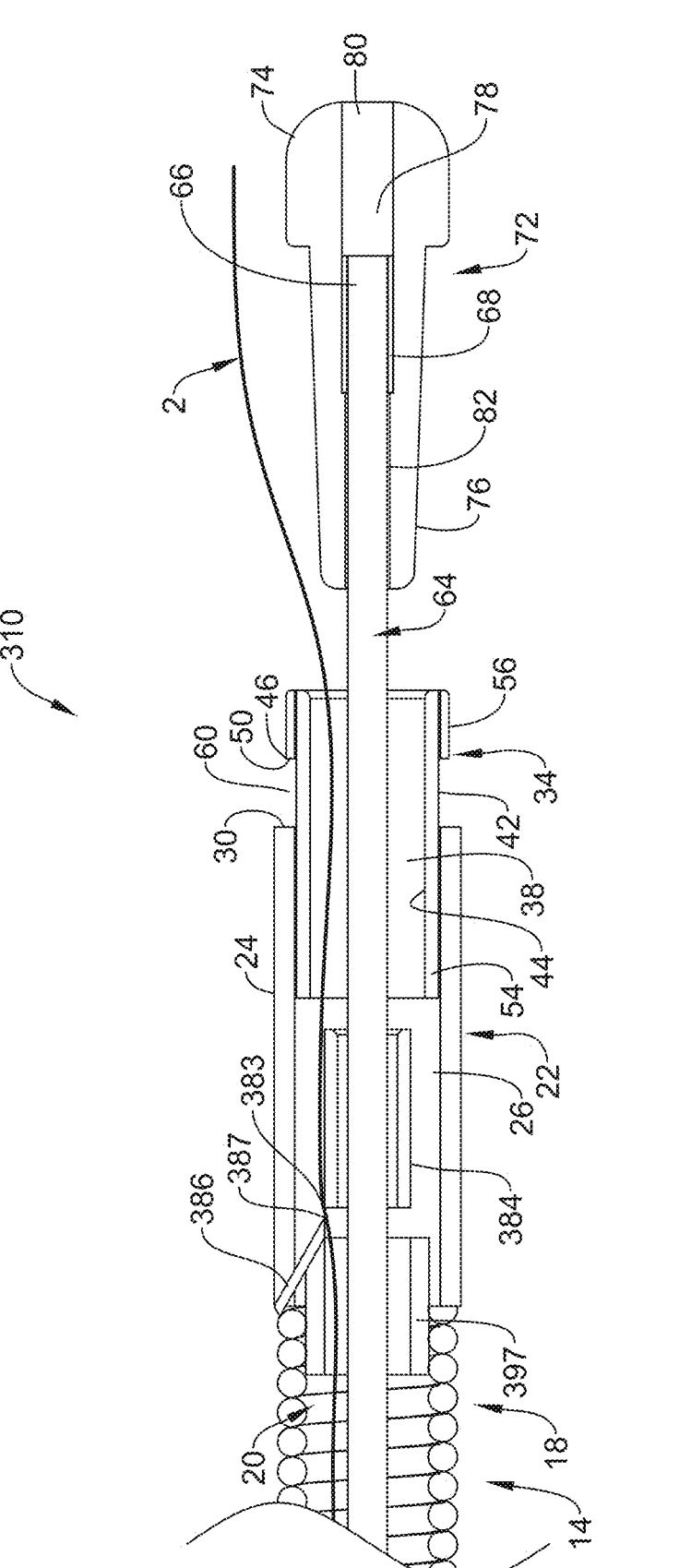
FIG. 17 is a side cross-sectional view of a portion of another embodiment of a medical device for applying a cinch to a suture including an alternative cutter configuration and showing a suture extending there through in a through-the-device configuration.

FIG. 17 depicts another example medical device 310 that may be similar in form and function to the other devices described therein, wherein like names and/or reference numbers indicate the same or similar structure and/or function as described elsewhere herein. While other components of the device/assembly remain largely the same, this embodiment includes a different configuration for the shear member 386 and the suture cutting member 384. The suture cutting member 384 may take the form of a tubular member on axis with the inner shaft 64, and the suture cutting member 384 may be releasably engaged/secured with the distal region 22, for example, with a frangible bond. A shear edge 383 may be defined and/or disposed on the proximal end of the suture cutting member 384. The suture cutting member 384 may receive the inner shaft 64. In this example, the shear member 386 is a blade and/or blade like member affixed to a tubular member 397, which may in turn be affixed to the shaft 14 (e.g. the distal region 22, proximal region 18, or both). An opening may be defined between the shear edge 383 of the cutting member 384 and the shear edge 387 of the shear member 386. Proximal retraction of the inner shaft 64 causes the distal portion 68 of the inner shaft 64 to engage the suture cutting member 384, and release and/or break the frangible bond. Further proximal retraction of the inner shaft 64 may bring together the shear edge 383 and shear edge 387, shifting them from an open to a closed configuration, and which engage to shear/cut the suture 2.

As such, use of the device 310 may be similar to that of other embodiments of devices described herein. For example, the device 310 may start in a first configuration, where the proximal portion 54 of the outer cinch member 34 is disposed within the lumen 26 and is engaged with the distal region 22 of the elongated shaft 14 such that a gap 60 is defined between the proximally facing shoulder surface 50 and the distally facing end surface 30. The inner shaft 64 may go through the first, second, third, and fourth stages of proximal movement, as described herein. When doing so, the cinch (e.g., including the outer cinch member 34 and the inner cinch member 72) may be applied to the suture 2, the gap 60 between the proximally facing shoulder 50 and the distal end surface 30 may close into a second configuration, the suture cutting member 384 may shift from the open to the closed configuration, to cut the suture 2, and the cinch (e.g., including the outer cinch member 34 and the inner cinch member 72) may be released.

While FIG. 17 depicts the suture 2 being arranged in a "through the device" configuration, other configurations are contemplated including a "side saddle" configuration. When doing so, the wall of the distal region 22 of the shaft 14 may include a cutout (e.g., similar to the cutout 25 as shown in FIG. 1) through which the suture 2 can be passed. In some instances, the suture 2 may pass through the suture cutting member 384 and then through the cutout and/or opening (not shown) in the wall of the distal region 22 of the shaft 14. Proximal retraction of the inner shaft 64 may bring together the shear edge 383 and shear edge 87, which engage to shear/cut the suture 2.

Figure 18:
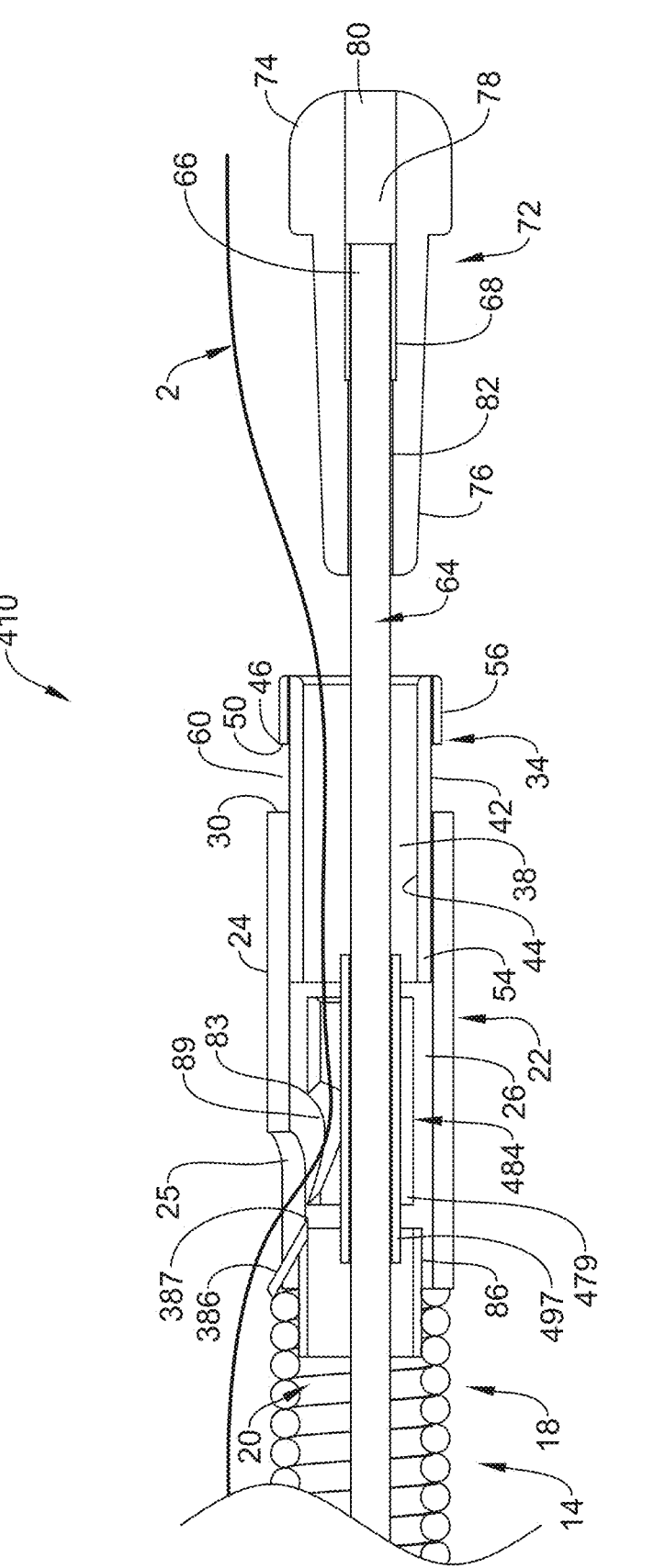
FIG. 18 is a side cross-sectional view of a portion of another embodiment of a medical device for applying a cinch to a suture including an alternative cutter configuration and showing a suture extending there through in a side saddle configuration.

FIG. 18 depicts another example medical device 410 that may be similar in form and function to the other devices described therein, wherein like names and/or reference numbers indicate the same or similar structure and/or function as described elsewhere herein. While other components of the device/assembly remain largely the same, this embodiment includes a different configuration for the suture cutting member 484. The suture cutting member 484 may include an inner tube 497 and outer tube 479 attached to the inner tube 497. The inner tube 497 may be releasably engaged/secured to a shear member 86, for example, with a frangible bond. The outer tube 479 may be arranged off-axis or otherwise in a non-coaxial manner with the inner tube 497 so that an opening is defined between the two tubes so that a suture 2 may pass there through. The suture cutting member 484 may also include a cutout or skive 89, for example at the proximal end thereof, that may help guide the suture toward and/or through an opening 25 in the tube wall 24 of the distal region 22 of the shaft 14 in a side saddle arrangement. In this example, the shear member 86 may include a blade like member 386 having a shear edge 387. Proximal retraction of the inner shaft 64 may bring together the shear edge 83 and shear edge 387, which engage to shear/cut the suture 2. For example, the inner shaft 64 may be retracted until the enlarged section 66 contacts the distal end of the inner tube 497. Further proximal retraction of the inner shaft 64 may break and/or release the frangible bond between the inner shaft 497 and the shear member 86, and allow the shear edge 83 of the suture cutting member 484 to come together with the shear edge 387, from an open to a closed configuration, and cut/shear the suture 2.

As such, use of the device 410 may be similar to that of other embodiments of devices described herein. For example, the device 410 may start in a first configuration, where the proximal portion 54 of the outer cinch member 34 is disposed within the lumen 26 and is engaged with the distal region 22 of the elongated shaft 14 such that a gap 60 is defined between the proximally facing shoulder surface 50 and the distally facing end surface 30. The inner shaft 64 may go through the first, second, third, and fourth stages of proximal movement, as described herein. When doing so, the cinch (e.g., including the outer cinch member 34 and the inner cinch member 72) may be applied to the suture 2, the gap 60 between the proximally facing shoulder 50 and the distal end surface 30 may close into a second configuration, the suture cutting member 484 may shift from the open to the closed configuration, to cut the suture 2, and the cinch (e.g., including the outer cinch member 34 and the inner cinch member 72) may be released.

Figure 19:
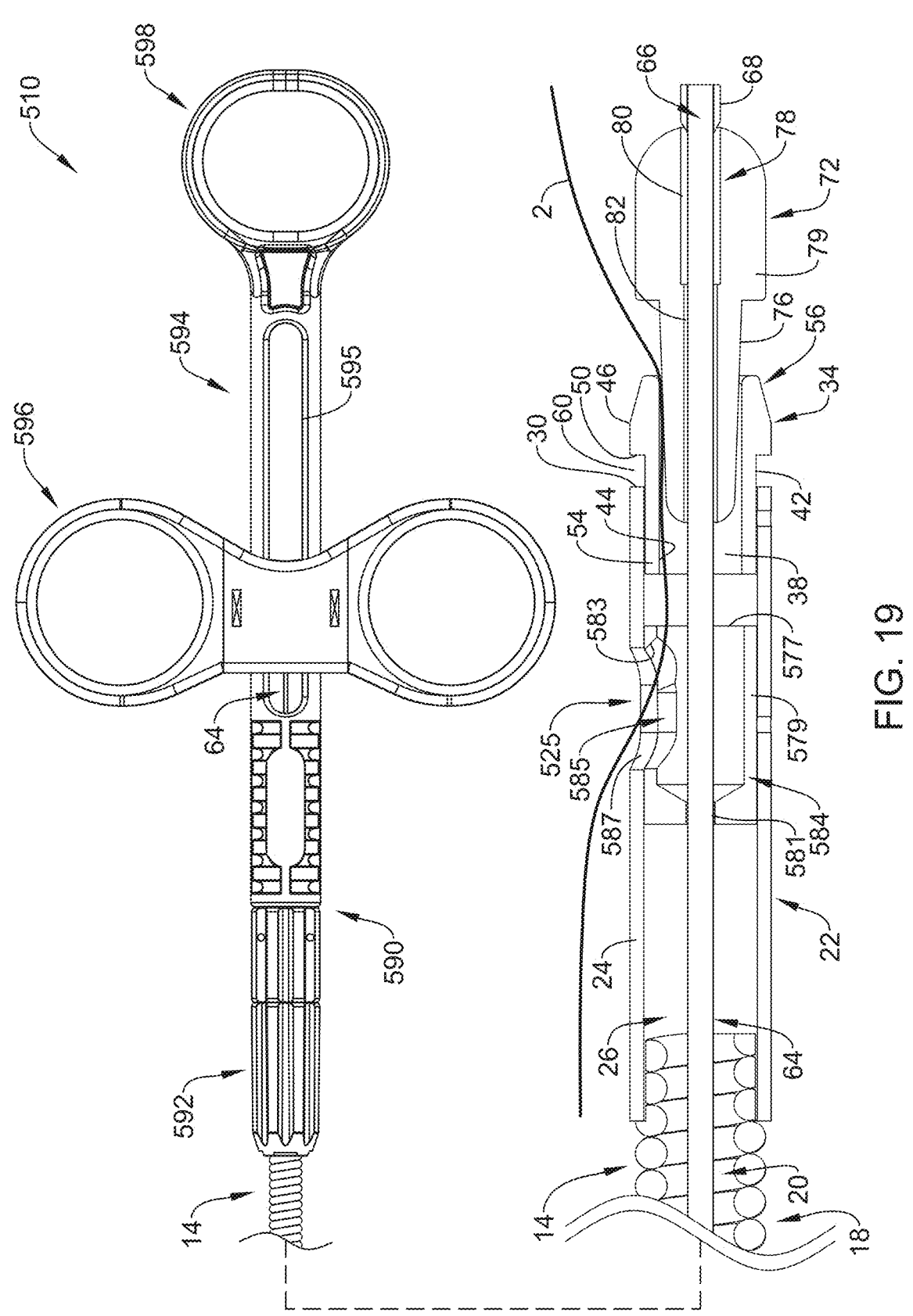
FIG. 19 is a side cross-sectional view of a portion of another embodiment of a medical device for applying a cinch to a suture including an alternative cutter configuration and showing a suture extending there through in a side saddle configuration.

FIG. 19 illustrates another example medical device 510 that may be similar in form and function to the other devices described therein, wherein like names and/or reference numbers indicate the same or similar structure and/or function as described elsewhere herein. While other components of the device/assembly remain largely the same, this embodiment includes a different configuration for a suture cutting member 584 and a shear edge 583. In particular, in this configuration, the device 510 does not include a separate "union" and/or shear member, (for example, unions or shear members 86, 386) as provided in some of the embodiments herein. Rather, in this embodiment, structure of the distal region 22 of the shaft 14 defines a shear edge 587 that works in conjunction with a shear edge 583 on the suture cutting member 584 to cut the suture 2. In some respects, the distal region 22 of the shaft 14 is and/or defines a shear member within the lumen that defines a distally facing shear edge 587 that works in conjunction with a proximally facing shear edge 583 on the suture cutter.

For example, in this embodiment, the distal region 22 of the shaft 14 includes a side opening and/or window and/or cutout 525 that extends through the wall 24 thereof. As in some other embodiments, the cutout 525 may provide access to the lumen 26 through the wall 24, for example, such that a suture 2 may extend there through when the device 510 is used in a "side saddle" arrangement—where the suture extends from within the lumen 26 through the cutout 525, and a proximal portion of the suture extends external of the device 510 along the proximal region 18 of the shaft 14, as discussed herein. Additionally, in this embodiment, the cutout 525 defines a distally facing shear edge 587. The shear edge 587 defined by the cutout 525 in the distal region 22 of the shaft may be designed to work with the shear edge 583 of the suture cutting member 584 such that a suture 2 disposed between the shear edges 587 and 583 may be cut or sheared when the shear edges 587 and 583 come together and/or close.

The suture cutting member 584 may be largely the same or similar in form and function to the suture cutting member 84 described herein. The suture cutting member 584 member is disposed within the lumen 26 of the distal region 22 of the shaft 14, and the inner shaft 64 may extend through the suture cutting member 84. The suture cutting member 584 may be a generally tubular member including a wall 579 having an outer diameter and defining a lumen having a distal opening 577 and a proximal opening 581. In at least some instances, the distal opening 577 may be designed so that the inner shaft 64 can pass there through. The proximal opening 581 may be designed so that the inner shaft 64 can extend at least partially there through. However, the proximal opening 581 may be narrower than the distal opening 577. For example, the proximal opening 581 may be sized so that the enlarged section 68 of the inner shaft 64 may not be able to pass through the proximal opening 581. This may provide an engagement mechanism between the inner shaft 64 and the suture cutting member 584 such that proximal retraction of the inner shaft 64 (e.g., relative to the suture cutting member 584) may include engagement of the enlarged section 68 of the inner shaft 64 with the suture cutting member 584 (e.g., at a location adjacent to the proximal opening 81) such that further proximal movement of the inner shaft 64 may result in the suture cutting member 584 translating (e.g., proximally) within the lumen 26 of the shaft 14.

In general, the suture cutting member 584, in conjunction with the shear edge 583, may be designed to terminate and/or otherwise cut a suture used with the device 510. For example, a cutout 585 may be formed in the wall 579 of the suture cutting member 584. A shear edge 583 may be defined along the cutout 585. In at least some instances, the shear edge 583 may face in a generally proximal direction. The shear edge 583, in conjunction with the shear edge 587 defined in the distal region 22 of the shaft 14 may be used to cut a suture 2 as described herein.

In this embodiment, the outer diameter of the suture cutting member 84 is sized to fit within, and selectively movable and/or slidable within the lumen 26 of the distal region 22 of the shaft 14. In at least some embodiments, it may be desirable to have a relatively tight tolerance fit between the inner diameter (e.g. lumen 26) of the distal region 22 of the shaft 14, and the outer diameter of the suture cutting member 84. This may provide for a better and/or tighter suture cutting arrangement between the shear edges 587, 583 as they are moved toward one another to cut the suture. The suture cutting member 584 may be designed to shift between a first or open configuration and a second closed configuration. For example, a first open configuration is depicted in FIG. 19, where an opening is defined between the shear edge 583 of the suture cutting member 584 and the shear edge 587 of the distal region 22 of the shaft 14. A suture 2 may extend through this opening between the edges 583 and 587 in this configuration. In the second, or closed configuration, the shear edge 583 of the suture cutting member 584 is brought adjacent to and/or engages and/or passes proximally by the shear edge 587 to close the opening and cut the suture. In some instances, the suture cutting member 584 may be releasably engaged and/or coupled to the distal region 22 of the shaft 14, for example with a releasable and/or frangible bond. For example, the two structures may be fixedly secured to each other with a releasable and/or frangible bond while in the open configuration as shown in FIG. 19. Thus, in an original state, where the releasable and/or frangible bond is engaged and/or intact, the suture cutting member 584 may be in the open configuration. Proximal retraction of the inner shaft 64 may bring the enlarged section 68 of the inner member 64 into contact with a surface of the suture cutting member 584 (e.g., adjacent to the proximal opening 581) so that further proximal retraction of the inner shaft 64 may break and/or sever and/or release and/or disengage the releasable and/or frangible bond and allow the suture cutting member 84 to be shifted (e.g., moved proximally) from the open configuration toward and/or into the closed configuration and cut/shear the suture 2.

As such, use of the device 510 may be similar to that of other embodiments of devices described herein. For example, the device may start in a first configuration, where the proximal portion 54 of the outer cinch member 34 is disposed within the lumen 26 and is engaged with the distal region 22 of the elongated shaft 14 such that a gap 60 is defined between the proximally facing shoulder surface 50 and the distally facing end surface 30. The inner shaft 64 may go through the first, second, third, and fourth stages of proximal movement, as described herein. When doing so, the cinch (e.g., including the outer cinch member 34 and the inner cinch member 72) may be applied to the suture 2, the gap 60 between the proximally facing shoulder 50 and the distal end surface 30 may close in a second configuration, the suture cutting member 584 may shift from the open to the closed configuration, to cut the suture 2, and the cinch (e.g., including the outer cinch member 34 and the inner cinch member 72) may be released.

The medical device 510 of FIG. 19 is also shown as including an alternative handle and/or user interface 590 that may be designed and/or configured for user interaction to provide relative movement between the elongated shaft 14 and the inner shaft 64. The user interface 590 is similar in many respects to the user interface 90 shown and discussed herein with reference to FIG. 1, with some modification. In the embodiment shown in FIG. 19, the user interface 590 incudes a distal portion 592, a proximal portion 594, and a slider portion 596 that is disposed about and/or along the proximal portion 594. The distal portion 592 is connected to the proximal end of the elongated shaft 14, and the proximal portion 594 is connected to and extends proximally from the distal portion 592. The slider portion 596 is connected to the proximal end of the inner shaft 64. The slider portion 596 is disposed on and longitudinally movable and/or slidable over and/or along the proximal portion 594. As such, the user interface 590 may provide for longitudinal movement of the inner shaft 64 relative to the elongate shaft 14 by actuation of the slider 596 relative to the proximal portion 594. In some instances, the slider portion 596 may be designed to slide along a groove or slot 595 formed in the proximal portion 594. In this embodiment, the slider portion 596 includes two finger loops designed to accommodate the fingers of a user (e.g., an index finger, a middle finger, combinations thereof, or other fingers) so that a user can use the finger loops to engage the slider portion 596 to slide it along the proximal portion 596 in order to shift the inner shaft 64 relative to the elongated shaft 14.

The proximal end of the proximal portion 594 may also be configured for user engagement, and as such, may include a structure or a shape that may enhance user engagement, grip and/or comfort. For example, the proximal end of the proximal portion 594 may include a loop 598, such as a thumb loop or the like. For example, a user may engage the user interface 590 by inserting a thumb into the thumb loop 598, and inserting one or more fingers into one or more of the finger loops of the slider portion 596.

The user interface 590 may include a number of additional features. For example, a removable slider stop (not shown) may be disposed along and/or within the channel 595, which may prevent undesired movement of the slider member 596 (e.g., during shipping and/or storage). In addition or in the alternative, the user interface 590 may include one or more stops, locks, spring members, detents, indexing, markings or the like for visualizing, controlling and/or limiting longitudinal movement of the slider member 596. While not shown in this embodiment, the user interface 590 may also optionally include a suture exit port similar to the suture exit port, for example similar to the suture exit port 93 described above and shown in FIG. 1. The user interface 590 as described herein may be included and/or used with any of the various embodiments of medical devices disclosed herein.

Figure 20:
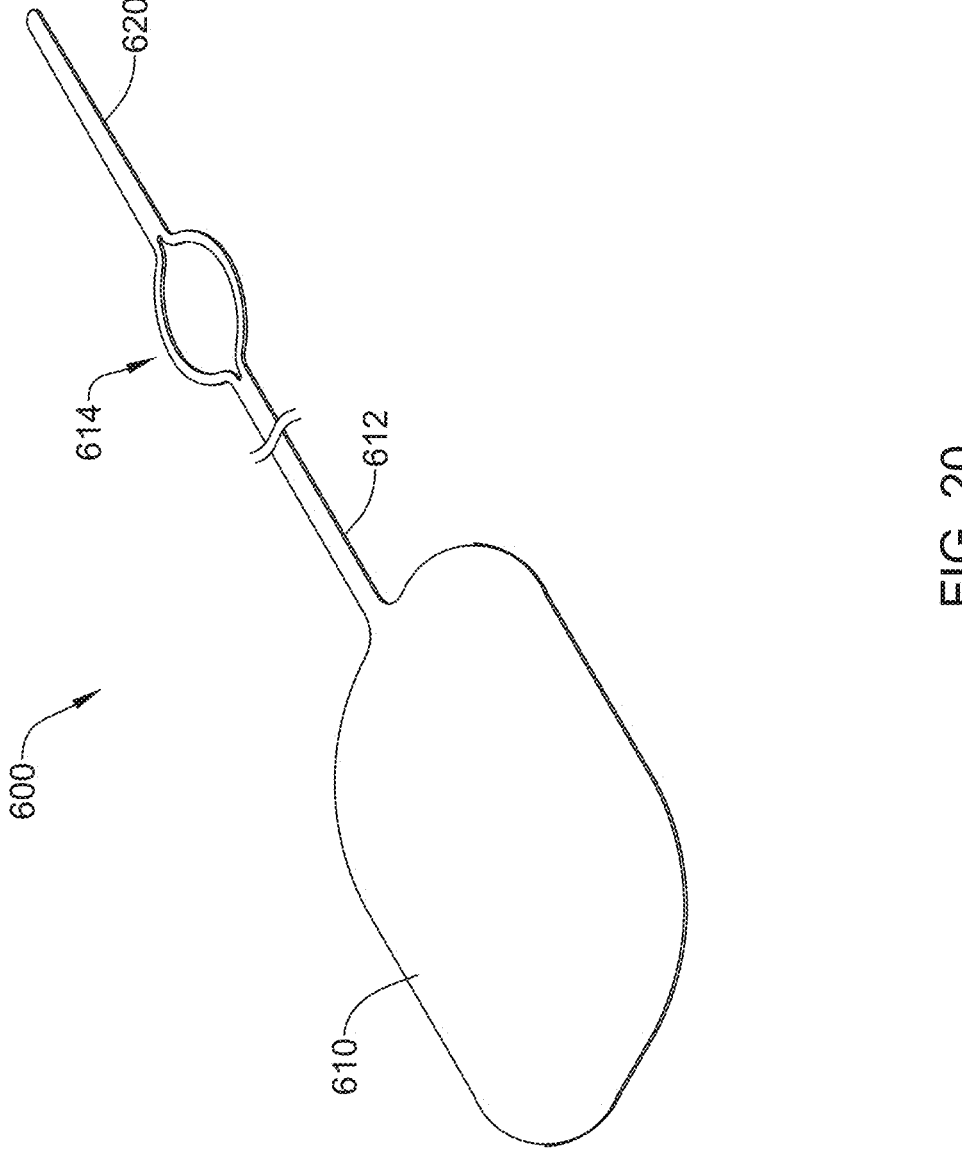
FIG. 20 is a perspective view of an example suture guide tab that may be used for loading and/or threading a suture through any of the embodiments of the medical devices disclosed herein.

FIG. 20 shows an example suture guide device and/or mechanism that may be used for loading and/or threading the suture 2 through any of the embodiments of the medical devices disclosed herein. FIG. 20 shows and example embodiment of a suture guide tab 600. The suture guide tab 600 includes: a handle portion 610; a proximal shaft portion 612 extending distally from the handle portion 610; a loop portion 614 extending distally from the proximal shaft portion 612; and a distal shaft portion 620 extending distally from the loop portion 614. The suture guide tab 600 may include or be made of one or more metals, polymers, and/or composite or layered or reinforced structures thereof, including any of those disclosed herein. In some example embodiments, the structure of the suture guide tab 600 may be cut from a sheet of polymeric material, and may be of monolithic and/or unitary construction. For example, in some embodiments, the suture guide tab 600 may be a monolithic structure cut from a sheet of polyimide material.

Figure 21:
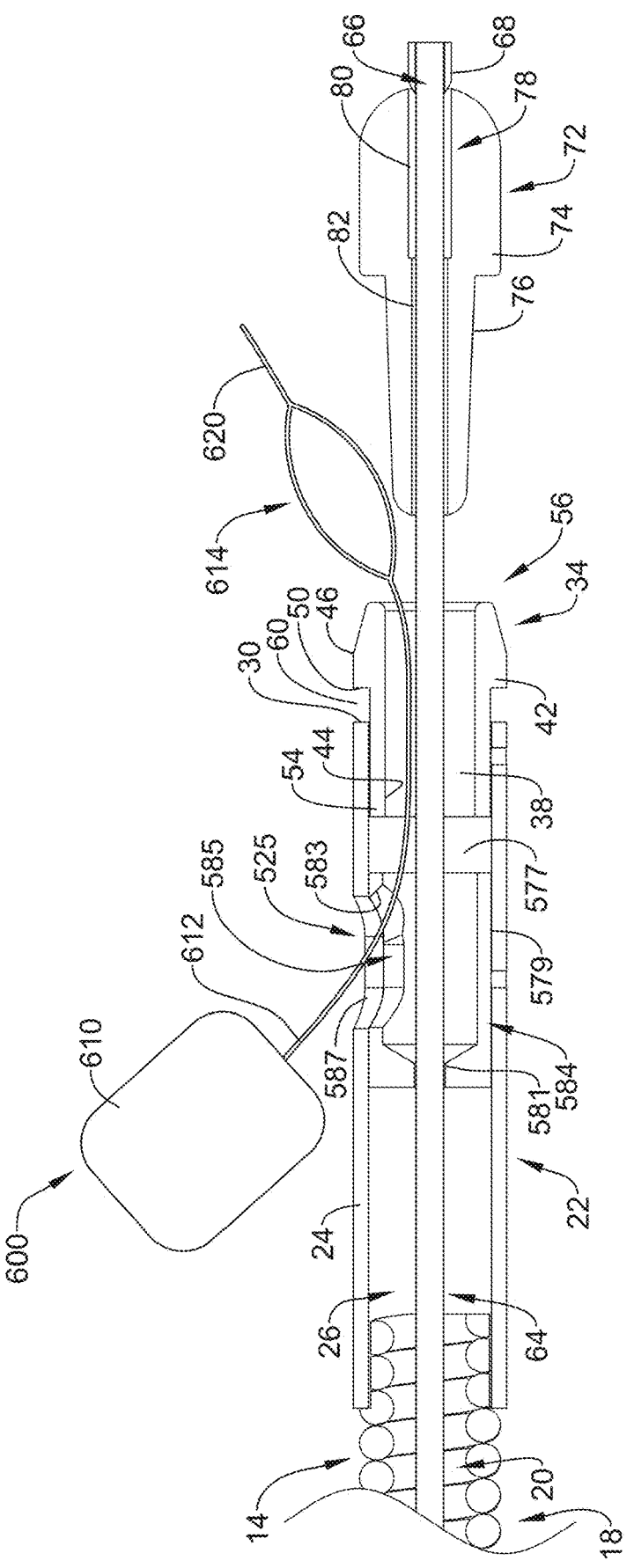
FIG. 21 is a side cross-sectional view of a portion of the medical device of FIG. 19, showing the suture guide tab of FIG. 20 inserted in a suture pathway through the medical device.
Figure 22:
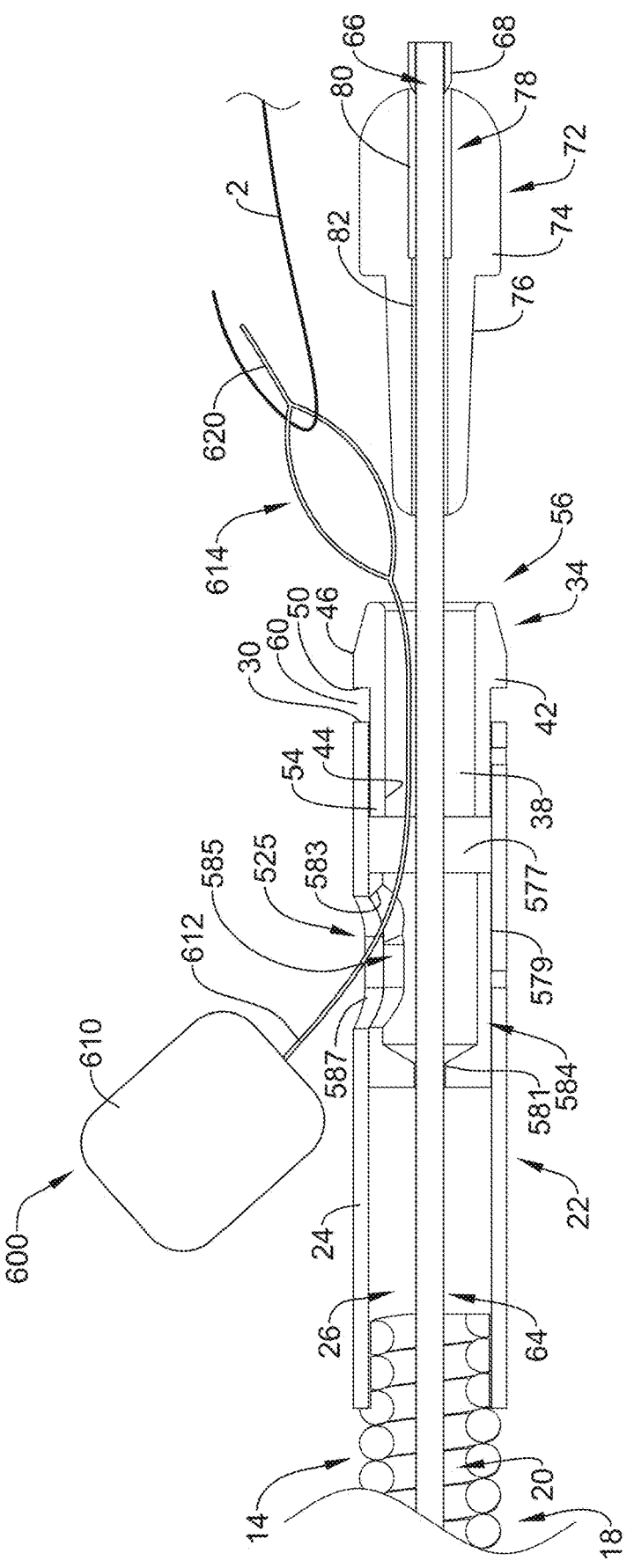
FIG. 22 shows a suture fed through a loop portion of the suture guide tab in preparation for pulling the suture through the pathway of the medical device.
Figure 23:
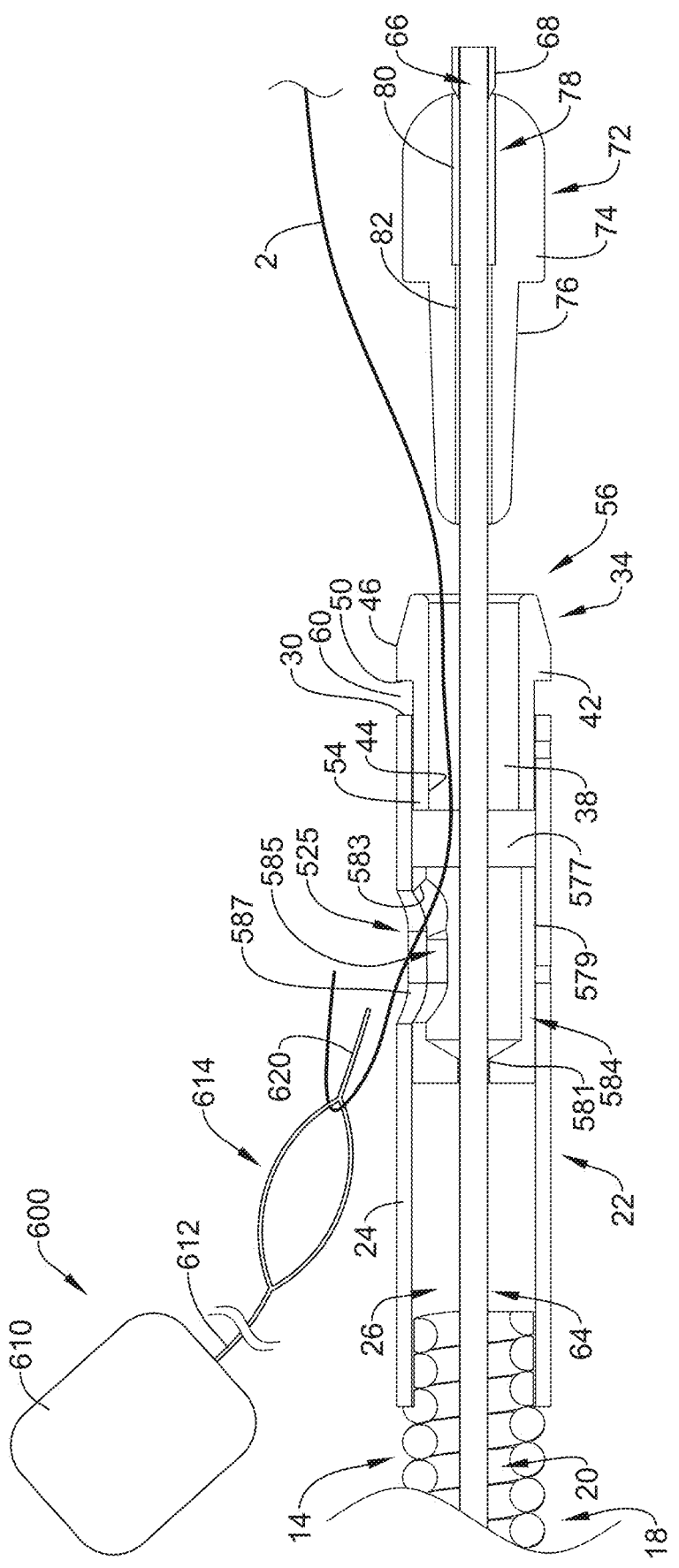
FIG. 23 the suture guide tab pulled back through the medical device to pull the suture back through the pathway through the medical device.

FIGS. 21-23 show an example of use of the suture guide tab 600 for loading and/or threading the suture 2 through the medical device 510 (e.g. of FIG. 19). As a general proposition, the suture guide tab 600 may be threaded through the device 510 along a desired pathway, and then used to pull the suture 2 back through the device along that desired pathway. As shown in FIG. 21, the suture guide tab 610 may be inserted in the desired pathway for the suture 2 to extend through the device 510. In this example, it will be desirable to load the suture in a "side saddle" arrangement—where the suture 2 is loaded into the distal region of the device 510, and then extends from within the device 510 through the cutout 525, and extends external of the device 510 along the proximal region 18 of the shaft 14. For example, as shown, the suture guide tab 600 may be inserted and/or extend through a pathway in the device that extends through the cutout 525 in the distal region 22, through the cutout 585 of the suture cutting member 584, through the lumen of the suture cutting member 584 into and through the lumen 26 of the distal region 22, into and through the bore 38 of the outer cinch member 34, and out between the outer and inner cinch members 34 and 72. The suture guide tab 600 may be so disposed through the pathway in the device 510 such that the handle 610 is disposed proximally and externally alongside the medical device 510 (e.g. adjacent and/or proximal of the cutout 525). The proximal shaft 612 extends from the handle and is disposed within the pathway through the device 510. The loop portion 614 is disposed distally of the pathway and externally alongside the medical device 510 (e.g. adjacent and/or distal and/or between the outer and inner cinch members 34 and 72). The distal shaft portion 620 extends distally of the loop portion 614. The distal shaft portion 620 may aid in navigating the suture guide tab 600, and in particular, the loop portion 614, through the pathway of the medical device 510.

As shown in FIG. 22, a suture 2 may then be fed through the loop portion 614. As shown in FIG. 23, the suture guide tab 600 may then be pulled back through the device 510 to pull the suture 2 back through the pathway through the device 510. As such, the suture guide tab 610 may be used to help guide and/or load the suture 2 through the device 510. Once the suture 2 is pulled through the device 510 as desired, the suture guide tab 610 can be removed from the suture 2, and the device 510 may be advanced over the suture 2 down to the suturing/defect site where it is desirable to apply a cinch to the suture 2, and/or cut the suture as desired. When doing so, the suture 2 remains inserted in the pathway through the device 510 until the cinch is applied and the suture is cut. It should be understood that the suture guide tab 600 as described herein may be included and/or used with any of the various embodiments of medical devices disclosed herein to aid in threading a suture through the desired pathway of the particular device.

The materials that can be used for the various components of the medical devices disclosed herein may include those commonly associated with medical devices. Any of the devices, members and/or components of members or devices disclosed herein may be made from a metal, metal alloy, polymer (some examples of which are disclosed below), a metal-polymer composite, ceramics, combinations thereof, and the like, or other suitable material or composites of materials. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments polymers can be blended with a liquid crystal polymer (LCP). For example, the mixture can contain up to about 6 percent LCP.

Some examples of suitable metals and metal alloys include stainless steel, such as 304V, 304L, 316LV, and 17-7 stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL®

400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A medical device for applying a cinch to a suture, the medical device comprising:
an elongated shaft having a distal end region and a distal end;
an outer cinch member secured to the distal end region of the elongated shaft with a frangible bond, wherein the outer cinch member is configured to shift between a first position and a second position upon breaking the frangible bond between the outer cinch member and elongated shaft;
an elongated inner shaft extending through and longitudinally movable within the elongated shaft and the outer cinch member; and
an inner cinch member engaged with a distal end section of the elongated inner shaft, the inner cinch member configured to be moved into engagement with the outer cinch member and to shift the outer cinch member from the first position toward the second position and thereby break the frangible bond.

2. The medical device of claim 1, wherein the elongated inner shaft is configured such that proximal longitudinal movement of the elongated inner shaft moves the inner cinch member into engagement with the outer cinch member.

3. The medical device of claim 1, wherein the outer cinch member is moved proximally from the first position to the second position.

4. The medical device of claim 1, wherein the elongated inner shaft is configured such that proximal longitudinal movement of the elongated inner shaft shifts the outer cinch member from the first position toward the second position.

5. The medical device of claim 1, wherein the elongated inner shaft is configured such that proximal longitudinal movement of the elongated inner shaft releases the frangible bond between the outer cinch member and the distal end region of the elongated shaft.

6. The medical device of claim 1, wherein movement of the outer cinch member into the second position causes the frangible bond between the outer cinch member and the distal end region of the elongated shaft to be released.

7. The medical device of claim 1, further including a suture cutting member disposed within the distal end region of the elongated shaft, and wherein the elongated inner shaft is configured to engage the suture cutting member for cutting the suture.

8. The medical device of claim 1, wherein the elongated inner shaft is configured such that a first stage of proximal longitudinal movement of the elongated inner shaft moves the inner cinch member into engagement with the outer cinch member, and a second stage of proximal longitudinal movement of the elongated inner shaft shifts the outer cinch member toward the second position.

9. The medical device of claim 8, wherein the elongated inner shaft is configured such that a third stage of proximal movement of the elongated inner shaft disengages the elongated inner shaft from the inner cinch member.

10. The medical device of claim 9, further including a suture cutting member disposed within the distal end region of the elongated shaft, and the elongated inner shaft is configured such that a fourth stage of proximal movement of the elongated inner shaft engages the elongated inner shaft with the suture cutting member.

11. The medical device of claim 1, further comprising:
a cutout defined in the distal end region of the elongated shaft defining a distally facing shear edge; and
a suture cutting member disposed within the distal end region of the elongated shaft and including a proximally facing shear edge, the suture cutting member having an open configuration wherein the proximally facing shear edge is disposed distally of the distally facing shear edge to define an opening between the proximally facing shear edge and the distally facing shear edge, and wherein the suture cutting member is configured to shift toward a closed configuration where the proximally facing shear edge has moved proximally relative to the distally facing shear edge such that the opening is closed.

12. The medical device of claim 11, wherein the elongated inner shaft is configured such that proximal longitudinal movement of elongated inner shaft shifts the suture cutting member from the open configuration toward the closed configuration.

13. The medical device of claim 11, wherein in the open configuration the suture cutting member is engaged with the distal end region of the elongated shaft with a bond.

14. A medical device, comprising:
a catheter shaft having a distal end region;
an outer cinch member secured to the distal end region of the catheter shaft with a frangible bond and configured to shift between a first position and a second position upon breaking the frangible bond between the outer cinch member and catheter shaft;
an inner shaft extending through the catheter shaft and through the outer cinch member, the inner shaft having a distal end section; and
an inner cinch member configured to be engaged with the distal end section of the inner shaft, the inner cinch member configured to shift the outer cinch member from the first position toward the second position.

15. The medical device of claim 14, wherein the outer cinch member is moved proximally from the first position to the second position.

16. The medical device of claim 14, wherein the inner shaft is configured such that proximal longitudinal movement of the inner shaft releases the frangible bond between the outer cinch member and the distal end region of the catheter shaft.

17. The medical device of claim 14, wherein movement of the outer cinch member into the second position causes the frangible bond between the outer cinch member and the distal end region of the catheter shaft to be released.

* * * * *